United States Patent
Katsuki et al.

(10) Patent No.: US 8,217,184 B2
(45) Date of Patent: Jul. 10, 2012

(54) PROCESS FOR PRODUCING OPTICALLY ACTIVE CIS-SILYL OLEFIN OXIDE COMPOUND

(75) Inventors: Tsutomu Katsuki, Fukuoka (JP); Kazuhiro Matsumoto, Fukuoka (JP); Takuya Kubo, Fukuoka (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 349 days.

(21) Appl. No.: 12/721,986

(22) Filed: Mar. 11, 2010

(65) Prior Publication Data

US 2010/0305338 A1 Dec. 2, 2010

(30) Foreign Application Priority Data

May 26, 2009 (JP) .................................. 2009-126105

(51) Int. Cl.
*C07D 301/12* (2006.01)
*C07F 7/08* (2006.01)
(52) U.S. Cl. ..................................................... 549/215
(58) Field of Classification Search .................... 549/215
See application file for complete search history.

(56) References Cited

PUBLICATIONS

Wong et al., "Organocatalytic Oxidation. Asymmetic Epoxidation of Olefins Catalyzed by Chiral Ketones and Iminium Salts," Chem. Rev., 2008, pp. 3958-3987, vol. 108, American Chemical Society.
Shi, "Organocatalytic Asymmetric Epoxidation of Olefins by Chiral Ketones," Accounts of Chemical Research, 2004, pp. 488-496, vol. 37, No. 8, American Chemical Society.
Yang, "Ketone-Catalyzed Asymmetric Epoxidation Reactions," Accounts of Chemical Research, 2004, pp. 497-505, vol. 37, No. 8, American Chemical Society.
Warren et al., "Chiral Ketone-Catalyzed Asymmetric Epoxidation of 2,2-Disubstituted Vinylsilanes," J. Org. Chem., 1999, pp. 7675-7677, vol. 64, Americal Chemical Society.
Eisch et al., "Regiospecificity and Stereochemistry in the Hydralumination of Unsymmetrical Acetylenes. Controlled Cis or Trans Reduction of 1-Alkynyl Derivatives," J. Org. Chem., 1971, pp. 3520-3526, vol. 36, No. 23.
Katsuki, "The Synthesis of E-(2S,3S)-3-Trimethylsilylglycidol and its Conversion to (–)-Propranolol," Tetrahedron Letters, 1984, pp. 2821-2822, vol. 25, No. 26, Pergamon Press Ltd., Great Britain.
Matsumoto et al., "Construction of Pseudo-Heterochiral and Homochiral Di-μ-oxotitanium(Schiff base) Dimers and Enantioselective Epoxidation Using Aqueous Hydrogen Peroxide," Angew. Chem. Int. Ed., 2005, pp. 4935-4939, vol. 44, Wiley-VCH Verlag GmbH & Co. KGaA, Weinheim.
Kobayashi et al., "Remarkable Efficieny in the Catalytic Asymmetric Epoxidation of (E)-3-Trimethylsilyl-2-propen-l-ol," Synlett, Nov. 1991, pp. 811-813.

*Primary Examiner* — Bernard Dentz
(74) *Attorney, Agent, or Firm* — Oliff & Berridge, PLC

(57) ABSTRACT

The present invention provides an efficient production method of an optically active cis-silylolefin oxide compound useful as an intermediate for various compounds. A production method of an optically active cis-silylolefin oxide compound by subjecting an optically active cis-silylolefin compound to an asymmetric oxidation with a high enantioselectivity and a high chemical yield by utilizing as a catalyst, an optically active titanium complex of Formula (1), Formula (2):

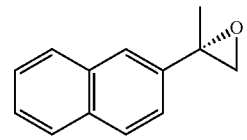

or the like.

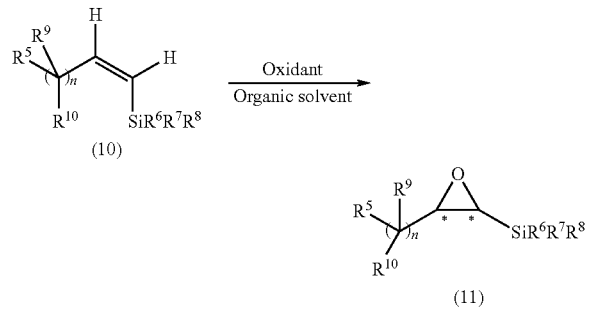

10 Claims, No Drawings

PROCESS FOR PRODUCING OPTICALLY ACTIVE CIS-SILYL OLEFIN OXIDE COMPOUND

TECHNICAL FIELD

The present invention relates to an efficient production method of an optically active cis-silylolefin oxide compound useful as an intermediate for various compounds.

BACKGROUND ART

Shi et al. have performed an epoxidation of a 2,2-di-substituted alkenylsilane using a catalyst derived from a sugar to obtain an epoxysilane with a selectivity of 94% ee, however, there is such a drawback that an equivalent catalyst is necessary (Non-patent Documents 1 to 4). From the introduction of a silyl group having a large steric hindrance into a vinyl-position, it is expected that the enantio-face selectivity is further enhanced, however, there is a problem that the large steric hindrance hinders the reaction (Non-patent Documents 5 and 6).

[Non-patent Document 1]
  Wong, O. A.; Shi, Y. Chem. Rev. 2008, 108, 3958.
[Non-patent Document 2]
  Shi, Y. Acc. Chem. Res. 2004, 37, 488.
[Non-patent Document 3]
  Yang, D. Acc. Chem. Res. 2004, 37, 497.
[Non-patent Document 4]
  Warren, J. D.; Shi, Y. J. Org. Chem. 1999, 64, 7675.
[Non-patent Document 5]
  Kobayashi, Y.; Ito, T.; Yamakawa, I.; Urabe, H.; Sato, F. *Synlett* 1991, 811.
[Non-patent Document 6]
  Katsuki, T. *Tetrahedron. Lett.* 1984, 25, 2821.

DISCLOSURE OF THE INVENTION

Problem to be Solved by the Invention

To provide a production method of an optically active cis-silylolefin oxide compound.

Means for Solving the Problem

As a result of assiduous research of a production method of an optically active cis-silylolefin oxide compound which was intended to overcome the above disadvantages, the inventors of the present invention found that by utilizing an optically active titanium complex as a catalyst, an optically active cis-silylolefin oxide compound can be produced with a high enantioselectivity and a high chemical yield, and completed the present invention.

[1]

Specifically, the present invention provides a production method of an optically active cis-silylolefin oxide compound of Formula (11):

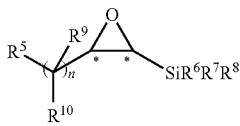
(11)

(where $R^5$ is a hydrogen atom, a $C_{1-22}$ alkyl group, a $C_{1-4}$ alkoxy group, or a $C_{6-10}$ aryl group (the aryl group is unsubstituted or is substituted with a halogen atom, a $C_{1-4}$ alkyl group, a $C_{6-10}$ aryl group (the aryl group is unsubstituted or is substituted with a halogen atom, a $C_{1-4}$ alkyl group or a $C_{1-4}$ alkoxy group) or a $C_{1-4}$ alkoxy group), $R^6$, $R^7$ and $R^8$ are each independently a hydrogen atom, a $C_{1-22}$ alkyl group or a $C_{6-10}$ aryl group (the aryl group is unsubstituted or is substituted with a halogen atom, a $C_{1-4}$ alkyl group or a $C_{1-4}$ alkoxy group), $R^9$ and $R^{10}$ are each independently a hydrogen atom, a $C_{1-6}$ alkyl group (the alkyl group may be optionally substituted with a halogen atom, a $C_{1-6}$ alkoxy group (the alkoxy group may be optionally substituted with a halogen atom) or a hydroxy group) or a $C_{6-14}$ aryl group (the aryl group may be optionally substituted with a halogen atom, a hydroxy group, a nitro group, a cyano group, a $C_{1-6}$ alkyl group (the alkyl group may be optionally substituted with a halogen atom, a $C_{1-6}$ alkoxy group (the alkoxy group may be optionally substituted with a halogen atom) or a hydroxy group) or a $C_{1-6}$ alkoxy group (the alkoxy group may be optionally substituted with a halogen atom)), n is an integer of 0 to 3, and the absolute configuration of the carbon atoms marked with "*" means (R) or (S)), characterized by subjecting a cis-silylolefin compound of Formula (10):

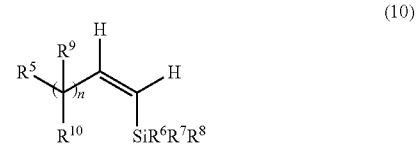
(10)

(where $R^5$, $R^6$, $R^7$, $R^8$, $R^9$, $R^{10}$ and n are the same as those defined above) to an asymmetric epoxidation with an oxidant using as a catalyst, an optically active titanium complex of any one of Formula (1), Formula (1'), Formula (2), Formula (2'), Formula (3), Formula (3'), Formula (4) and Formula (4'):

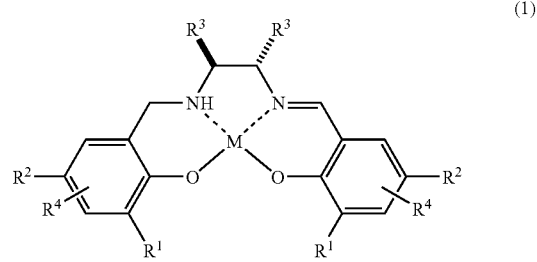
(1)

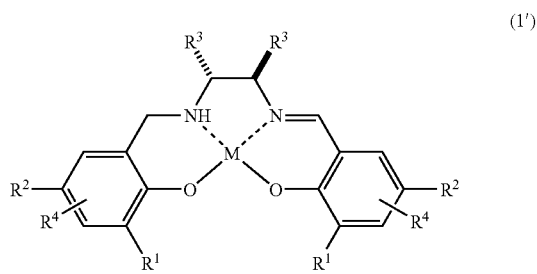
(1')

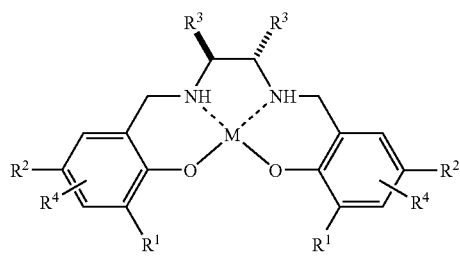
(2)

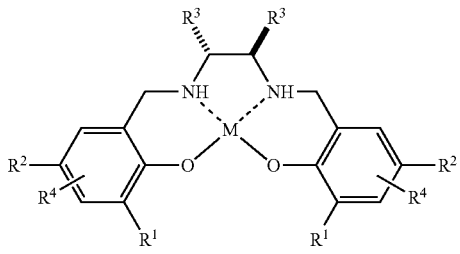
(2')

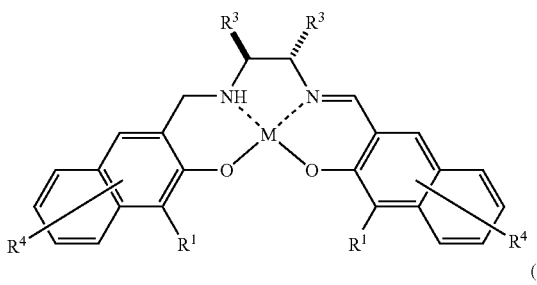
(3)

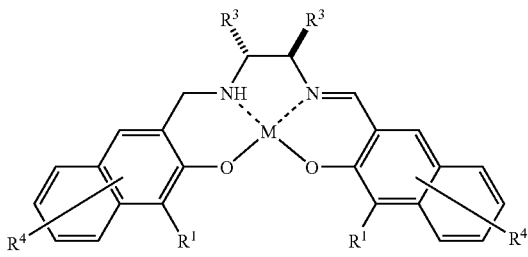
(3')

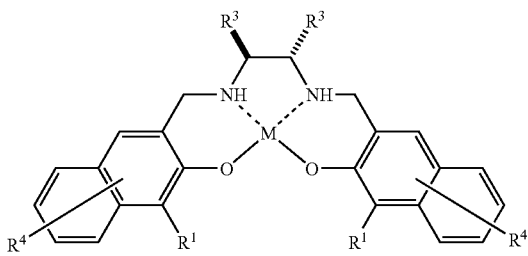
(4)

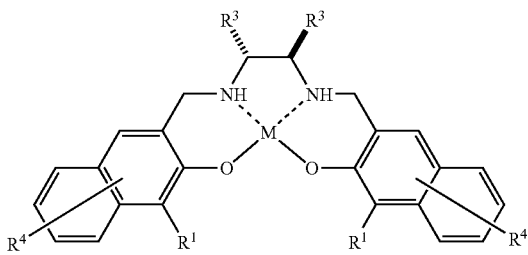
(4')

(where in Formula (1), Formula (1'), Formula (2), Formula (2'), Formula (3), Formula (3'), Formula (4) and Formula (4'), $R^1$ is a hydrogen atom, a halogen atom, a $C_{1-4}$ alkyl group, a $C_{1-4}$ alkoxy group, a $C_{6-12}$ aryloxy group or a $C_{6-22}$ aryl group (the aryl group may be optionally substituted with a $C_{1-4}$ alkyl group (the alkyl group may be optionally substituted with a halogen atom), a $C_{1-7}$ alkoxy group or a benzyloxy group, and is optically active or optically inactive); $R^2$ is a hydrogen atom, a halogen atom, a $C_{1-4}$ alkyl group, a $C_{1-4}$ alkoxy group, a $C_{6-12}$ aryloxy group or a $C_{6-18}$ aryl group; $R^3$ is a $C_{1-4}$ alkyl group, a $C_{6-18}$ aryl group, or a $C_{3-5}$ divalent group when two $R^3$s together form a ring; $R^4$s are each independently a hydrogen atom, a halogen atom, a $C_{1-4}$ alkyl group, a $C_{1-4}$ alkoxy group, a nitro group or a cyano group; and M is $TiJ^1J^2$ (in $TiJ^1J^2$: Ti is a titanium atom; $J^1$ and $J^2$ are each independently a halogen atom or $C_{1-4}$ alkoxide, $J^1$ and $J^2$ together are an oxygen atom, or $J^1$ and $J^2$ together form a ring to form a binuclear complex of Formula (5):

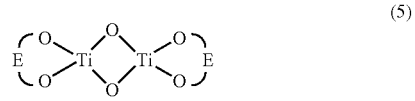
(5)

(where a partial structural formula O-E-O in Formula (5) is a formula of any one of Formula (6), Formula (6'), Formula (7), Formula (7'), Formula (8), Formula (8'), Formula (9) and Formula (9'):

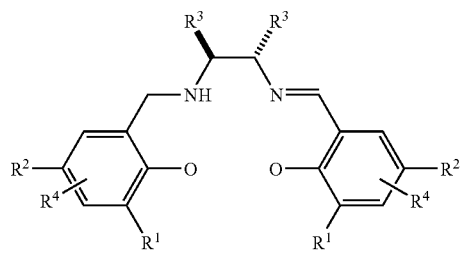
(6)

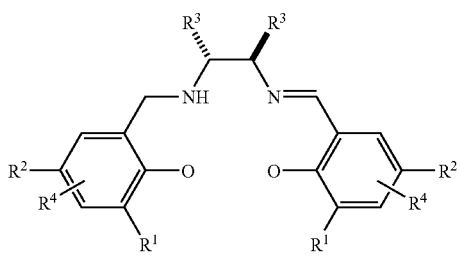
(6')

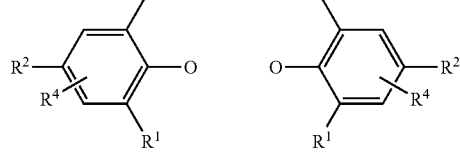
(7)

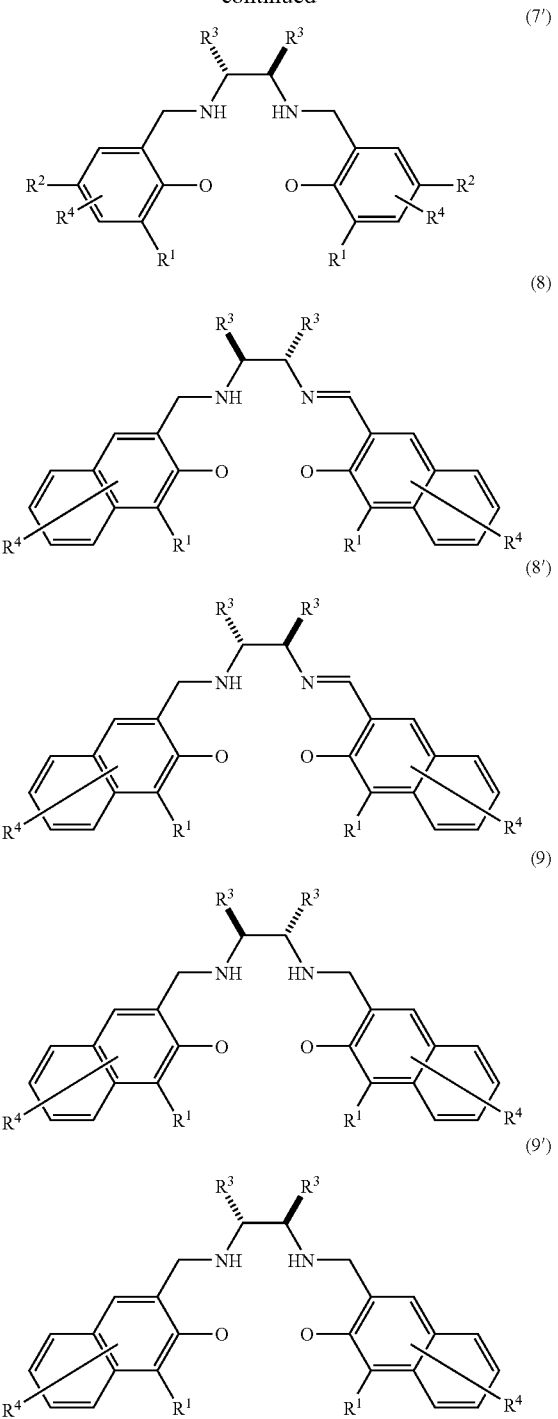

(where $R^1$, $R^2$, $R^3$ and $R^4$ in Formula (6), Formula (6'), Formula (7), Formula (7'), Formula (8), Formula (8'), Formula (9) and Formula (9') are the same as those defined above, and at this time, two partial structures O-E-O in Formula (5) are the same as each other))).

[2]

In the production method of an optically active cis-silylolefin oxide compound according to [1], the optically active titanium complex of any one of Formula (1), Formula (1'), Formula (2), Formula (2'), Formula (3), Formula (3'), Formula (4) and Formula (4') is an optically active titanium complex of any one of Formula (1), Formula (1'), Formula (2) and Formula (2'); $R^1$ is a phenyl group (the phenyl group may be optionally substituted with a $C_{1-4}$ alkyl group (the alkyl group may be optionally substituted with a halogen atom), a $C_{1-7}$ alkoxy group or a benzyloxy group); $R^2$ is a hydrogen atom; and two $R^3$s together are a $C_4$ divalent group.

[3]

In the production method of an optically active cis-silylolefin oxide compound according to [1], the optically active titanium complex of any one of Formula (1), Formula (1'), Formula (2), Formula (2'), Formula (3), Formula (3'), Formula (4) and Formula (4') is an optically active titanium complex of any one of Formula (3), Formula (3'), Formula (4) and Formula (4'); $R^1$ is a naphthyl group (the naphthyl group may be optionally substituted with a $C_{1-4}$ alkyl group (the alkyl group may be optionally substituted with a halogen atom), a $C_{1-7}$ alkoxy group or a benzyloxy group, and is optically active or optically inactive); $R^2$ is a hydrogen atom; and two $R^3$s together are a $C_4$ divalent group.

[4]

In the production method of an optically active cis-silylolefin oxide compound according to any one of [1] to [3], n is 0; and $R^5$ is a phenyl group (the phenyl group is unsubstituted or is substituted with a halogen atom, a $C_{1-4}$ alkyl group, a $C_{6-10}$ aryl group (the aryl group is unsubstituted or is substituted with a halogen atom, a $C_{1-4}$ alkyl group or a $C_{1-4}$ alkoxy group) or a $C_{1-4}$ alkoxy group).

[5]

In the production method of an optically active cis-silylolefin oxide compound according to any one of [1] to [4], the optically active titanium complex is a complex of Formula 1:

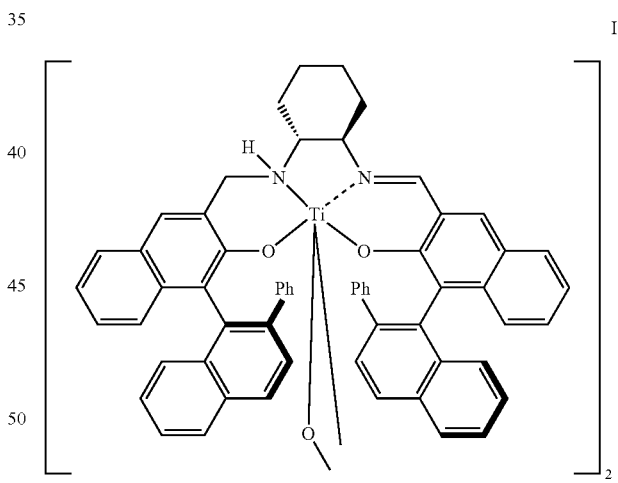

or an enantiomer of the complex.

[6]

In the production method of an optically active cis-silylolefin oxide compound according to any one of [1] to [5], the solvent to be used in the asymmetric epoxidation reaction is a halogen-based solvent, an aromatic hydrocarbon solvent, an ester solvent, an ether solvent, a nitrile solvent, an alcohol solvent or a mixture of these solvents.

[7]

In the production method of an optically active cis-silylolefin oxide compound according to any one of [1] to [5], the solvent to be used in the asymmetric epoxidation reaction is methylene chloride.

[8]

In the production method of an optically active cis-silylolefin oxide compound according to any one of [1] to [7], the oxidant to be used in the asymmetric epoxidation reaction is iodosobenzene, sodium hypochlorite, m-chloro-perbenzoic acid, Oxone (registered trademark of E.I. du Pont de Nemours and Company), hydrogen peroxide water, urea-hydrogen peroxide adduct (UHP), oxaziridine, N-methylmorpholine oxide (NMO), t-butyl hydroperoxide (TBHP), cumene hydroperoxide (CHP) or a mixture of these oxidants.

[9]

In the production method of an optically active cis-silylolefin oxide compound according to any one of [1] to [7], the oxidant to be used in the asymmetric epoxidation reaction is hydrogen peroxide water, urea-hydrogen peroxide adduct (UHP) or a mixture of these oxidants.

[10]

In the production method of an optically active cis-silylolefin oxide compound according to any one of [1] to [7], the oxidant to be used in the asymmetric epoxidation reaction is hydrogen peroxide water in a concentration of 1 to 100% by mass.

Effects of the Invention

According to the present invention, an optically active cis-silylolefin oxide compound useful as an intermediate for various compounds can be efficiently produced.

BEST MODES FOR CARRYING OUT THE INVENTION

In the present specification, "n" means normal; "i" means iso; "s" means secondary; "t" means tertiary; "c" means cyclo; "o" means ortho; "m" means meta; and "p" means para.

Hereinafter, the present invention will be described more in detail. The titanium complex used as a catalyst for subjecting a cis-silylolefin compound to an asymmetric epoxidation using an oxidant in the present invention is a complex of any one of Formula (1), Formula (1'), Formula (2), Formula (2'), Formula (3), Formula (3'), Formula (4) and Formula (4'):

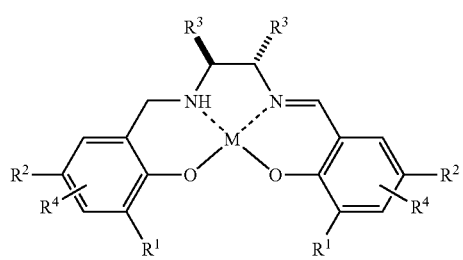

(1)

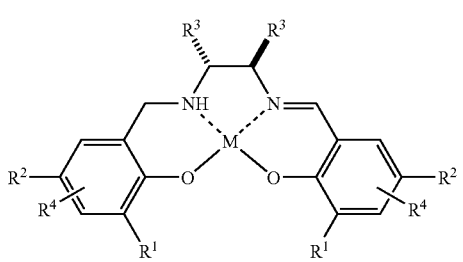

(1')

-continued

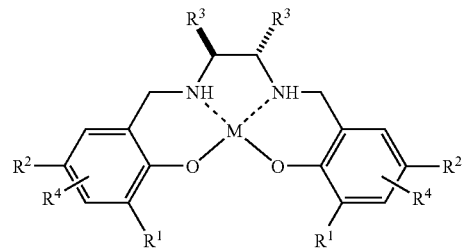

(2)

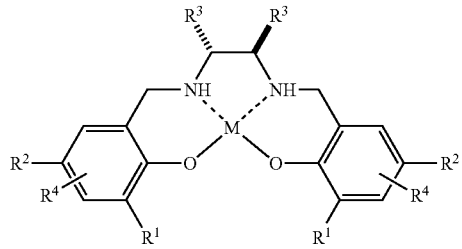

(2')

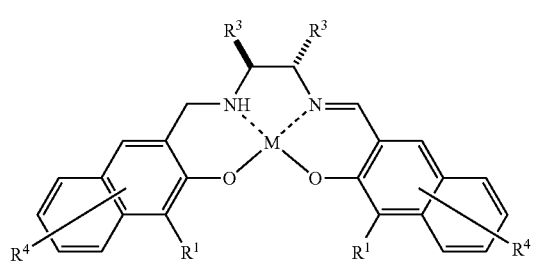

(3)

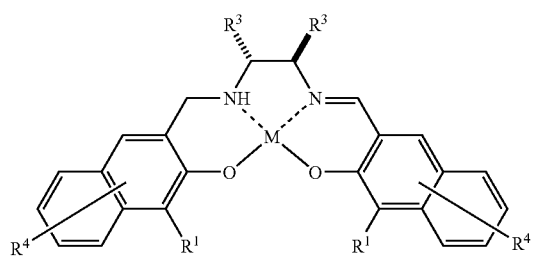

(3')

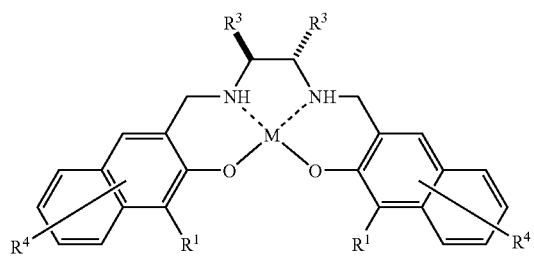

(4)

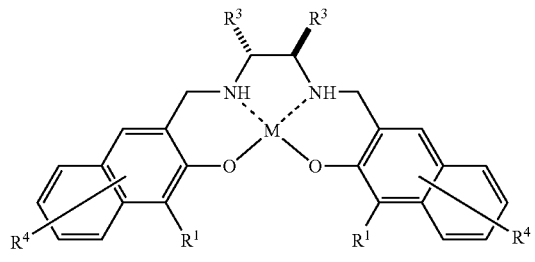

(4')

(where in Formula (1), Formula (1'), Formula (2), Formula (2'), Formula (3), Formula (3'), Formula (4) and Formula (4'), $R^1$ is a hydrogen atom, a halogen atom, a $C_{1-4}$ alkyl group, a $C_{1-4}$ alkoxy group, a $C_{6-12}$ aryloxy group or a $C_{6-22}$ aryl group (the aryl group may be optionally substituted with a $C_{1-4}$ alkyl group (the alkyl group may be optionally substituted with a halogen atom) or a $C_{1-7}$ alkoxy group, and is optically active or optically inactive), $R^2$ is a hydrogen atom, a halogen atom, a $C_{1-4}$ alkyl group, a $C_{1-4}$ alkoxy group, a $C_{6-12}$ aryloxy group or a $C_{6-18}$ aryl group, $R^3$ is a $C_{1-4}$ alkyl group, a $C_{6-18}$ aryl group, or a $C_{3-5}$ divalent group when two $R^3$s together form a ring, $R^4$s are each independently a hydrogen atom, a halogen atom, a $C_{1-4}$ alkyl group, a $C_{1-4}$ alkoxy group, a nitro group or a cyano group, and M is $TiJ^1J^2$ (in $TiJ^1J^2$: Ti is a titanium atom; $J^1$ and $J^2$ are each independently a halogen atom or $C_{1-4}$ alkoxide, $J^1$ and $J^2$ together are an oxygen atom, or $J^1$ and $J^2$ together form a ring to form a Formula (5):

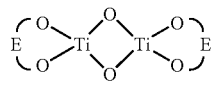
(5)

(where a partial structural formula O-E-O in Formula (5) is a formula of any one of Formula (6), Formula (6'), Formula (7), Formula (7'), Formula (8), Formula (8'), Formula (9) and Formula (9'):

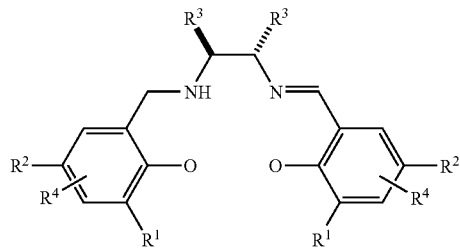
(6)

(6')

(7)

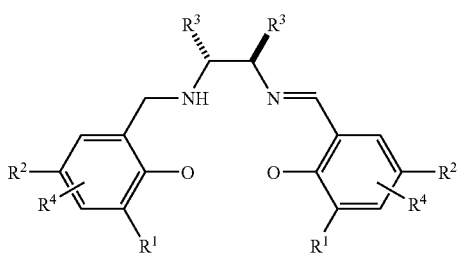

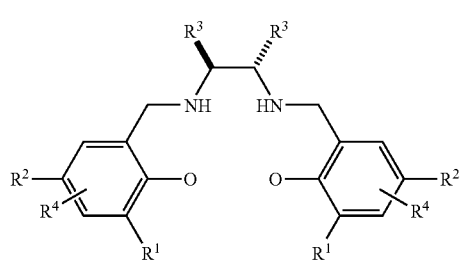

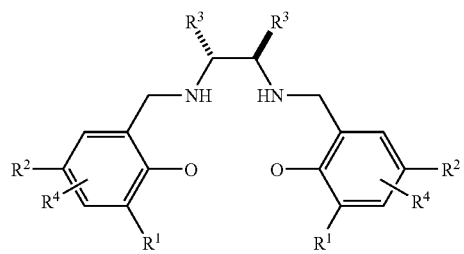
(7')

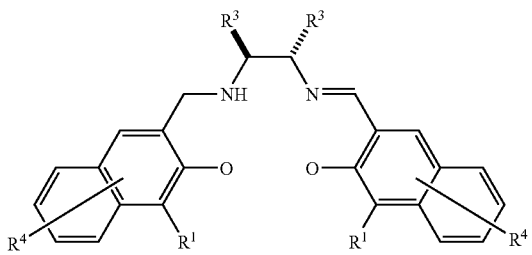
(8)

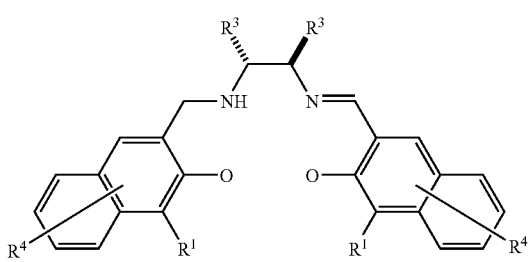
(8')

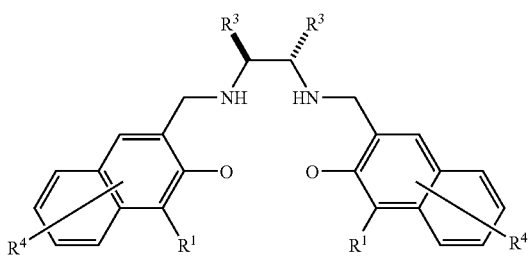
(9)

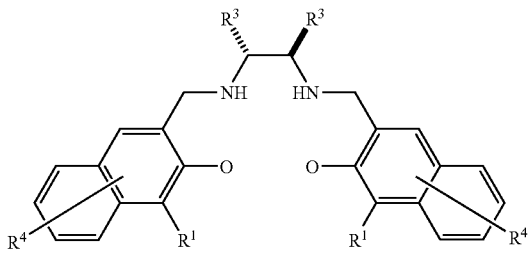
(9')

(where $R^1$, $R^2$, $R^3$ and $R^4$ in Formula (6), Formula (6'), Formula (7), Formula (7'), Formula (8), Formula (8'), Formula (9) and Formula (9') are the same as those defined above, and at this time, two partial structures O-E-O in Formula (5) are the same as each other). Here, the complex of Formula (1') is an enantiomer of the complex of Formula (1); the complex of Formula (2') is an enantiomer of the complex of Formula (2); the complex of Formula (3') is an enantiomer of the complex of Formula (3) and the complex of Formula (4') is an enantiomer of the complex of Formula (4). Among them, preferred is the complex of Formula (2), Formula (2') Formula (3) or Formula (3').

Each substituent in Formula (1), Formula (1'), Formula (2), Formula (2') Formula (3), Formula (3'), Formula (4) and Formula (4') is described.

$R^1$ in Formula (1), Formula (1'), Formula (2), Formula (2'), Formula (3), Formula (3'), Formula (4) and Formula (4') is, a hydrogen atom, a halogen atom, a $C_{1-4}$ alkyl group, a $C_{1-4}$ alkoxy group, a $C_6$-$C_{12}$ aryloxy group or a $C_{6-22}$ aryl group (the aryl group may be optionally substituted with a $C_{1-4}$ alkyl group (the alkyl group may be optionally substituted with a halogen atom) or a $C_{1-7}$ alkoxy group, and is optically active or optically inactive).

$R^1$ in Formula (1), Formula (1'), Formula (2), Formula (2'), Formula (3), Formula (3'), Formula (4) and Formula (4') is specifically described.

Examples of $R^1$, as the halogen atom, include a fluorine atom, a chlorine atom, a bromine atom and an iodine atom; as the $C_{1-4}$ alkyl group, include a methyl group, an ethyl group, an n-propyl group, an i-propyl group, an n-butyl group, an i-butyl group, an s-butyl group and a t-butyl group; as the $C_{1-4}$ alkoxy group, include a methoxy group, an ethoxy group, an n-propoxy group, an i-propoxy group, a c-propoxy group, an n-butoxy group, an i-butoxy group, an s-butoxy group, a t-butoxy group and a c-butoxy group; as the $C_{6-12}$ aryloxy group include a phenyloxy group, a 1-naphthyloxy group, a 2-naphthyloxy group, a 2-biphenyloxy group, a 3-biphenyloxy group and a 4-biphenyloxy group; and as the $C_{6-22}$ aryl group (the aryl group may be optionally substituted with a $C_{1-4}$ alkyl group (the alkyl group may be optionally substituted with a halogen atom), a $C_{1-7}$ alkoxy group or a benzyloxy group, and is optically active or optically inactive) include:

a phenyl group,
a 2-methylphenyl group, a 2-trifluoromethylphenyl group, a 4-methylphenyl group, a 2-ethylphenyl group, a 2-pentafluoroethylphenyl group, a 3,5-dimethylphenyl group, a 2-methoxyphenyl group, a 3-methoxyphenyl group, a 4-methoxyphenyl group, a 2-ethoxyphenyl group, a 2-i-propoxyphenyl group, a 2-benzyloxyphenyl group, a 3,5-dimethoxyphenyl group,
a 1-naphthyl group, a 2-naphthyl group,
a 2-biphenylyl group, a 3-biphenylyl group, a 4-biphenylyl group,
a 2-methyl-1-naphthyl group, a 2-phenyl-1-naphthyl group, a 2-methoxy-1-naphthyl group, a 2-[3,5-dimethylphenyl]-1-naphthyl group, a 2-[4-methylphenyl]-1-naphthyl group,
a 2-(o-biphenylyl)-1-naphthyl group,
a 2-(m-biphenylyl)-1-naphthyl group, and
a 2-(p-biphenylyl)-1-naphthyl group. Here, the $C_{6-22}$ aryl group may be either optically active or optically inactive.

$R^1$ in Formula (1), Formula (1'), Formula (2), Formula (2'), Formula (3), Formula (3'), Formula (4) and Formula (4') is preferably
a hydrogen atom, a fluorine atom, a chlorine atom, a bromine atom, an iodine atom,
a methyl group, an ethyl group, an n-propyl group, an i-propyl group, an n-butyl group, an i-butyl group, an s-butyl group, a t-butyl group,
a methoxy group, an ethoxy group, an n-propoxy group, an i-propoxy group, a c-propoxy group, an n-butoxy group, an i-butoxy group, an s-butoxy group, a t-butoxy group, a c-butoxy group, a phenyloxy group, a 1-naphthyloxy group, a 2-naphthyloxy group,
a phenyl group, a 2-methylphenyl group, a 2-trifluoromethylphenyl group, a 4-methylphenyl group, a 2-ethylphenyl group, a 3,5-dimethylphenyl group,
a 2-methoxyphenyl group, a 3-methoxyphenyl group, a 4-methoxyphenyl group, a 2-ethoxyphenyl group, a 2-i-propoxyphenyl group, a 2-benzyloxyphenyl group, a 3,5-dimethoxyphenyl group,
a 1-naphthyl group, a 2-naphthyl group, a 2-biphenylyl group, a 3-biphenylyl group, a 4-biphenylyl group,
a 2-phenyl-1-naphthyl group, a 2-methoxy-1-naphthyl group, a 2-(m-biphenylyl)-1-naphthyl group or a 2-(p-biphenylyl)-1-naphthyl group.

Among them, $R^1$ is more preferably
a phenyl group, a 2-methylphenyl group, a 2-trifluoromethylphenyl group, a 2-ethylphenyl group, a 2-methoxyphenyl group, a 2-benzyloxyphenyl group, a 1-naphthyl group, a 2-naphthyl group, a 2-biphenylyl group, a 2-phenyl-1-naphthyl group, a 2-methoxy-1-naphthyl group, a 2-(m-biphenylyl)-1-naphthyl group or a 2-(p-biphenylyl)-1-naphthyl group (the 2-phenyl-1-naphthyl group, the 2-methoxy-1-naphthyl group, the 2-(m-biphenylyl)-1-naphthyl group and the 2-(p-biphenylyl)-1-naphthyl group are optically active or optically inactive), and among them, $R^1$ is further preferably a phenyl group, a 2-methylphenyl group, a 2-trifluoromethylphenyl group, a 2-methoxyphenyl group, a 2-benzyloxyphenyl group or a 2-phenyl-1-naphthyl group.

$R^2$ in Formula (1), Formula (1'), Formula (2), Formula (2'), Formula (3), Formula (3'), Formula (4) and Formula (4') is a hydrogen atom, a halogen atom, a $C_{1-4}$ alkyl group, a $C_{1-4}$ alkoxy group, a $C_{6-12}$ aryloxy group or a $C_{6-18}$ aryl group.

$R^2$ in Formula (1), Formula (1'), Formula (2), Formula (2'), Formula (3), Formula (3'), Formula (4) and Formula (4') is specifically described.

Examples of $R^2$, as the halogen atom, include a fluorine atom, a chlorine atom, a bromine atom and an iodine atom; as the $C_{1-4}$ alkyl group, include a methyl group, an ethyl group, an n-propyl group, an i-propyl group, an n-butyl group, an i-butyl group, an s-butyl group and a t-butyl group; as the $C_{1-4}$ alkoxy group, include a methoxy group, an ethoxy group, an n-propoxy group, an i-propoxy group, a c-propoxy group, an n-butoxy group, an i-butoxy group, an s-butoxy group, a t-butoxy group and a c-butoxy group; as the $C_{6-12}$ aryloxy group include a phenyloxy group, a 1-naphthyloxy group, a 2-naphthyloxy group, a 2-biphenylyloxy group, a 3-biphenylyloxy group and a 4-biphenylyloxy group; and as the $C_{6-18}$ aryl group, include a phenyl group, a 3,5-dimethylphenyl group, a 4-methylphenyl group, a 1-naphthyl group, a 2-naphthyl group, a 2-biphenylyl group, a 2-phenyl-1-naphthyl group, a 2-methyl-1-naphthyl group, a 2-[3,5-dimethylphenyl]-1-naphthyl group, a 2-[4-methylphenyl]-1-naphthyl group and a 2-methoxy-1-naphthyl group.

$R^2$ in Formula (1), Formula (1'), Formula (2), Formula (2'), Formula (3), Formula (3'), Formula (4) and Formula (4') is preferably
a hydrogen atom, a fluorine atom, a chlorine atom, a bromine atom, an iodine atom, a methyl group, an ethyl group, an n-propyl group, an i-propyl group, an n-butyl group, a t-butyl group, a methoxy group,
a phenyloxy group, a 1-naphthyloxy group, a 2-naphthyloxy group,
a phenyl group, a 3,5-dimethylphenyl group, a 4-methylphenyl group, a 3,5-dimethoxyphenyl group, a 4-methoxyphenyl group, a 1-naphthyl group, a 2-naphthyl group, a 2-phenylphenyl group, a 3-biphenylyl group, a 4-biphenylyl group or a 2-methoxy-1-naphthyl group.

Among them, $R^2$ is more preferably a hydrogen atom, a fluorine atom, a chlorine atom, a bromine atom, an iodine atom, a methyl group, an ethyl group, an n-propyl group, an i-propyl group, an n-butyl group, a t-butyl group, a methoxy group, a phenyloxy group, a phenyl group, a 1-naphthyl group, a 2-naphthyl group or a 2-phenylphenyl group, and among them, $R^2$ is further preferably a hydrogen atom.

$R^3$ in Formula (1), Formula (1'), Formula (2), Formula (2'), Formula (3), Formula (3'), Formula (4) and Formula (4') is a $C_{1-4}$ alkyl group, a $C_{6-18}$ aryl group, or a $C_{3-5}$ divalent group when two $R^3$s together form a ring.

$R^3$ in Formula (1), Formula (1'), Formula (2), Formula (2'), Formula (3), Formula (3'), Formula (4) and Formula (4') is specifically described.

Examples of $R^3$, as the $C_{1-4}$ alkyl group, include a methyl group, an ethyl group, an n-propyl group, an i-propyl group, an n-butyl group, an i-butyl group, an s-butyl group and a t-butyl group; and as the $C_{6-18}$ aryl group, include a phenyl group, a 3,5-dimethylphenyl group, a 2,4,6-trimethylphenyl group, a 4-methylphenyl group, a 1-naphthyl group, a 2-biphenylyl group, a 2-phenyl-1-naphthyl group, a 2-methyl-1-naphthyl group, a 2-[3,5-dimethylphenyl]-1-naphthyl group, a 2-[4-methylphenyl]-1-naphthyl group and a 2-methoxy-1-naphthyl group; and when two $R^3$s together form a ring, they form a $C_{3-5}$ divalent group and examples of the divalent group include a trimethylene group and a tetramethylene group.

$R^3$ in Formula (1), Formula (1'), Formula (2), Formula (2'), Formula (3), Formula (3'), Formula (4) and Formula (4') is preferably a phenyl group, a 3,5-dimethylphenyl group, a 2,4,6-trimethylphenyl group, a 4-methylphenyl group or a tetramethylene group in which two $R^3$s are bonded to each other.

Among them, $R^3$ is more preferably
a tetramethylene group in which two $R^3$s are bonded to each other.

$R^4$ in Formula (1), Formula (1'), Formula (2), Formula (2'), Formula (3), Formula (3'), Formula (4) and Formula (4') is
a hydrogen atom, a halogen atom, a $C_{1-4}$ alkyl group, a $C_{1-4}$ alkoxy group, a nitro group or a cyano group.

$R^4$ in Formula (1), Formula (1'), Formula (2), Formula (2'), Formula (3), Formula (3'), Formula (4) and Formula (4') is specifically described.

Examples of $R^4$, as the halogen atom, include a fluorine atom, a chlorine atom, a bromine atom and an iodine atom;
as the $C_{1-4}$ alkyl group, include a methyl group, an ethyl group, an n-propyl group, an i-propyl group, an n-butyl group, an i-butyl group, an s-butyl group and a t-butyl group; and
as the $C_{1-4}$ alkoxy group, include a methoxy group, an ethoxy group, an n-propoxy group, an i-propoxy group, an n-butoxy group, an i-butoxy group, an s-butoxy group and a t-butoxy group.

$R^4$ in Formula (1), Formula (1'), Formula (2), Formula (2'), Formula (3), Formula (3'), Formula (4) and Formula (4') is preferably
a hydrogen atom, a fluorine atom, a chlorine atom, a bromine atom, a methyl group, an ethyl group, an n-propyl group, an i-propyl group, an n-butyl group, an i-butyl group, an s-butyl group, a t-butyl group, a methoxy group, an ethoxy group, an n-propoxy group, an i-propoxy group, an n-butoxy group, an i-butoxy group, an s-butoxy group, a t-butoxy group, and
among them, $R^4$ is more preferably a hydrogen atom.

M in Formula (1), Formula (1'), Formula (2), Formula (2'), Formula (3), Formula (3'), Formula (4) and Formula (4') is $TiJ^1J^2$ (in $TiJ^1J^2$: Ti is a titanium atom; $J^1$ and $J^2$ are each independently a halogen atom or a $C_{1-4}$ alkoxide group, $J^1$ and $J^2$ together are an oxygen atom, or $J^1$ and $J^2$ together form a ring to form a binuclear complex of Formula (5):

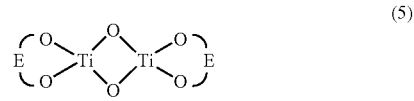

(5)

(where a partial structural formula O-E-O in Formula (5) is a formula of any one of Formula (6), Formula (6'), Formula (7), Formula (7'), Formula (8), Formula (8'), Formula (9) and Formula (9'):

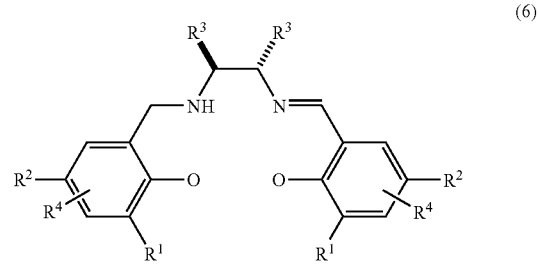

(6)

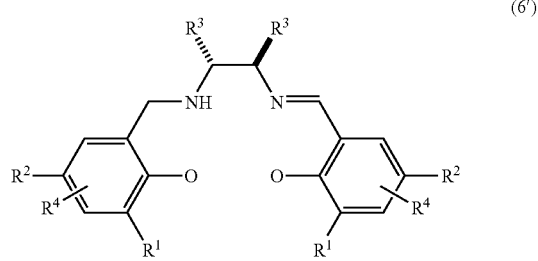

(6')

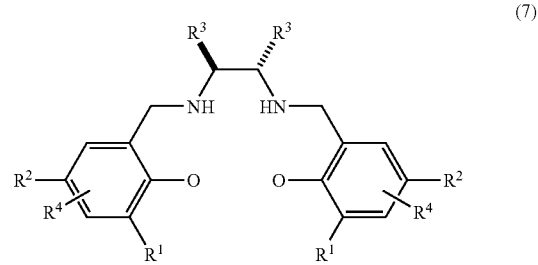

(7)

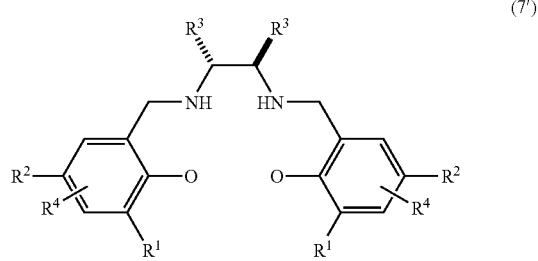

(7')

-continued

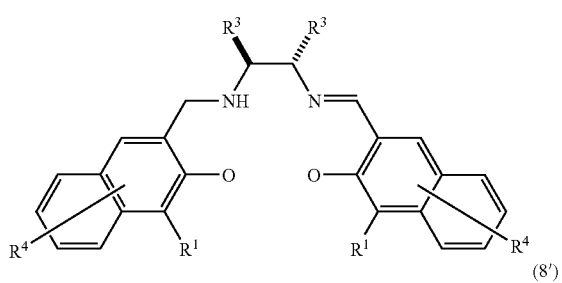

(8)

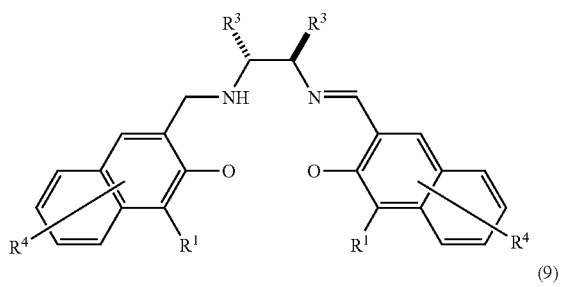

(8')

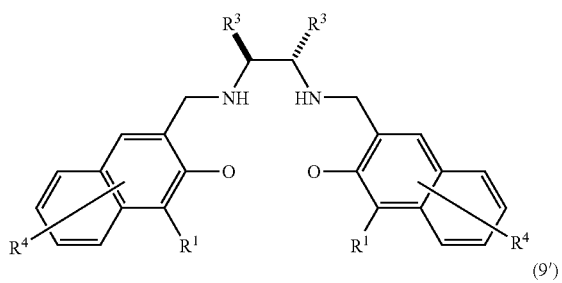

(9)

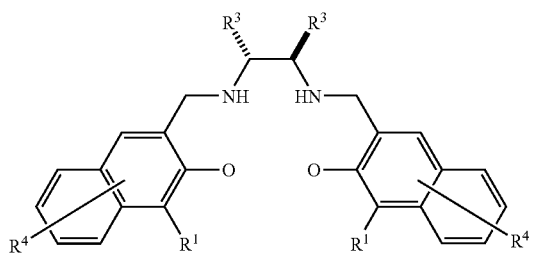

(9')

(where $R^1$, $R^2$, $R^3$ and $R^4$ in Formula (6), Formula (6'), Formula (7), Formula (7'), Formula (8), Formula (8'), Formula (9) and Formula (9') are the same as those defined above, and at this time, two partial structures O-E-O in Formula (5) are the same as each other).

Here, when $J^1$ and $J^2$ together are an oxygen atom, Formula (1), Formula (1'), Formula (2), Formula (2'), Formula (3), Formula (3'), Formula (4) and Formula (4') become as the whole structure of the molecule, a mononuclear oxotitanium complex, and when $J^1$ and $J^2$ together form a ring to form a divalent group of Formula (5), Formula (1), Formula (1'), Formula (2), Formula (2'), Formula (3), Formula (3'), Formula (4) and Formula (4') become as the whole structure of the molecule, a μ-oxotitanium (b+1) nuclear complex which is a multinuclear complex.

In addition, when Formula (1), Formula (1'), Formula (2), Formula (2'), Formula (3), Formula (3'), Formula (4) and Formula (4') are the oxotitanium complex or the μ-oxotitanium (b+1) nuclear complex, the optically active titanium complex of the present invention may be the oxotitanium complex or a mixture of μ-oxotitanium (b+1) nuclear complexes in a state in which b is any one of 1 to 10.

Examples of the preferred case of $J^1$ and $J^2$ include a case where $J^1$ and $J^2$ together are an oxygen atom and a case where $J^1$ and $J^2$ together form a ring to form a binuclear complex of Formula (5).

Further, there is described the preferred combination of substituents and the structure of the whole molecule with respect to the optically active titanium complex of the present invention by dividing the titanium complex into two types such as an optically active titanium salalen complex of Formula (1), Formula (1'), Formula (3) or Formula (3') and a titanium salan complex of Formula (2), Formula (2'), Formula (4) or Formula (4').

In the optically active titanium salalen complex of Formula (1), Formula (1'), Formula (3) and Formula (3'), $J^1$ and $J^2$ together form a ring to form a divalent group of Formula (5), and in Formula (5), b is preferably 1. In this case, Formula (1), Formula (1'), Formula (3) and Formula (3') become as the structure of the whole molecule, a μ-oxotitanium binuclear complex of Formulae (18) and (18'):

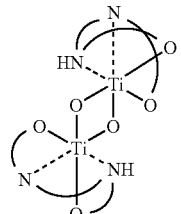

(18)

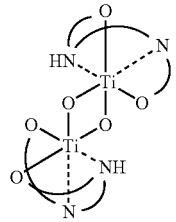

(18')

(where O—NH—N—O is Formula (19) in Formula (1), Formula (19') in Formula (1'), Formula (20) in Formula (2) and Formula (20') in Formula (2'):

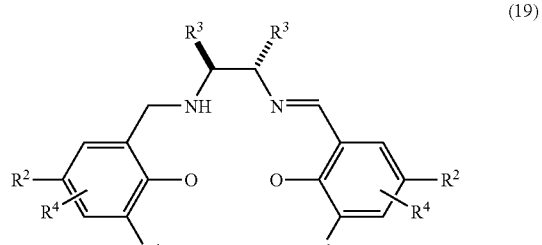

(19)

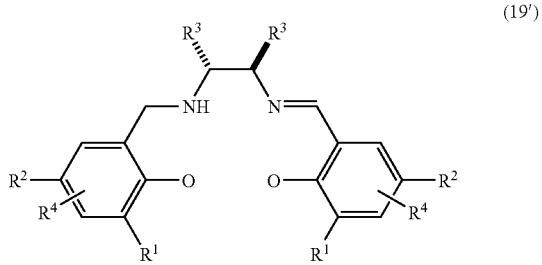

(19')

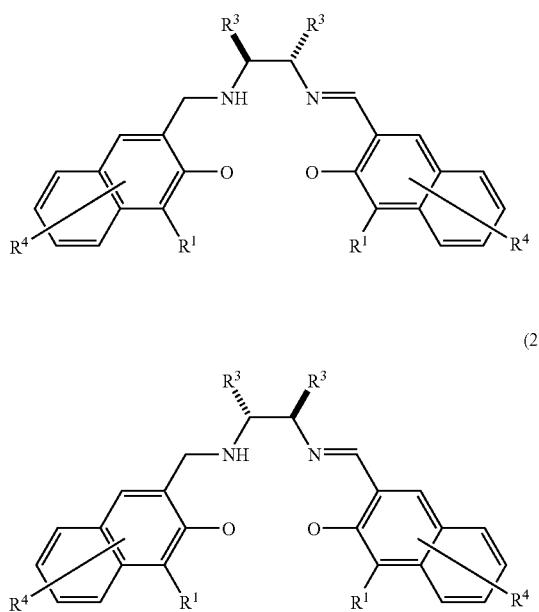

(20)

(20')

(where R¹, R², R³ and R⁴ are the same as those defined above) and the complex of Formula (18') is an enantiomer of the complex of Formula (18)).

A particularly preferred combination of substituents among the optically active titanium salalen complexes and the structure of the whole molecule thereof are described.

The particularly preferred optically active titanium salalen complexes are those of Formula (18) and Formula (18') that are a (aRSΔ, aRSΔ)-di-μ-oxotitanium binuclear complex and a (aSRΛ, aSRΛ)-di-μ-oxotitanium binuclear complex in which a partial structure O—NH—N—O in Formulae (18) and (18') is Formula (21), Formula (21'), Formula (22) or Formula (22'):

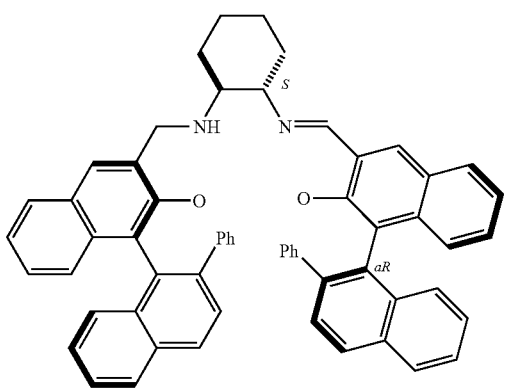

(21)

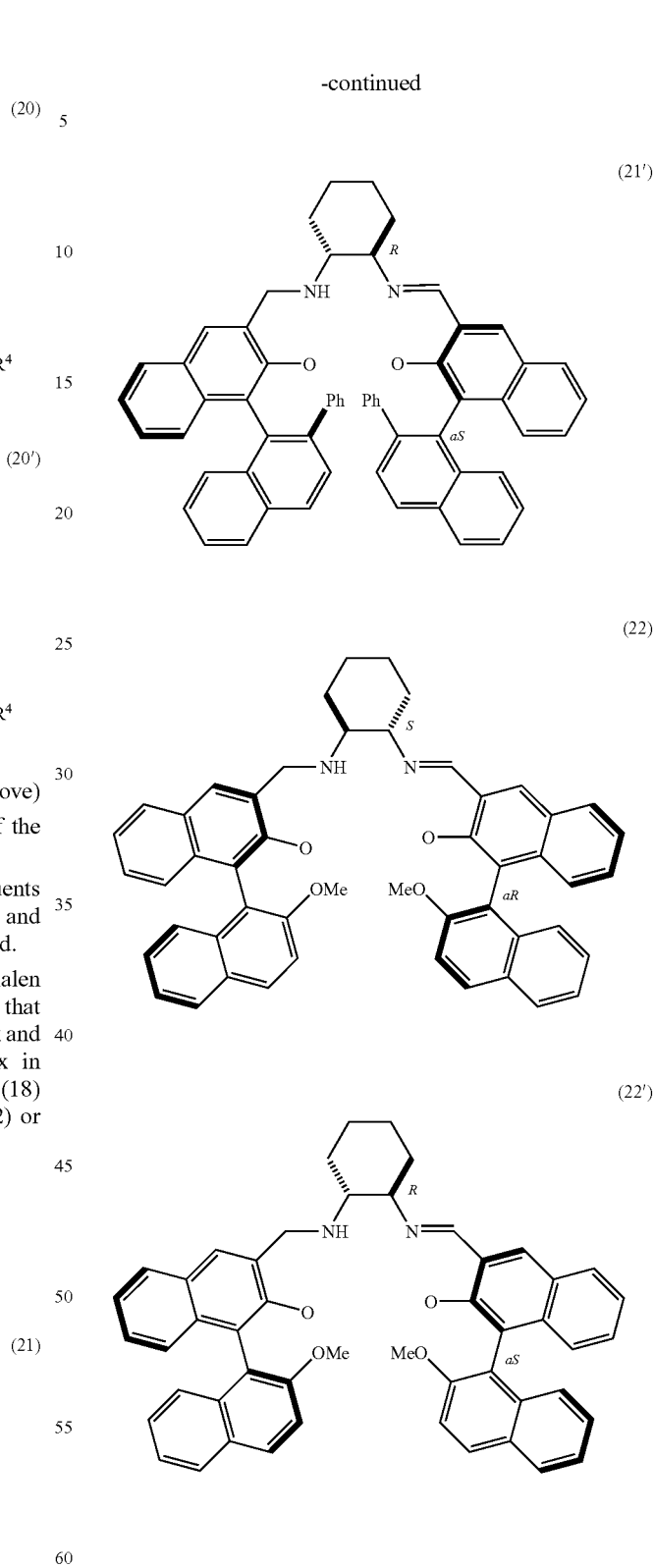

Examples of a particularly preferred combination of substituents in the optically active titanium salan complex of Formula (2), Formula (2'), Formula (4) and Formula (4') include mononuclear oxotitanium complexes and μ-oxotitanium (b+1) nuclear complexes (b is an integer of 1 to 10) of Formula (31), Formula (31'), Formula (32) and Formula (32'):

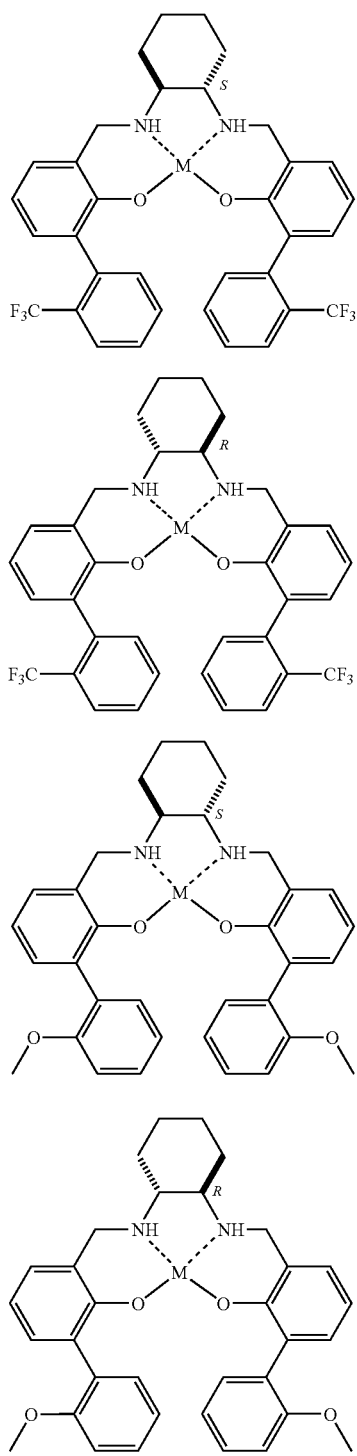

(where M is TiJ$^1$J$^2$, and J$^1$ and J$^2$ together are an oxygen atom or together form a ring to form a divalent group of Formula (5).

In Formula (5), b is an integer of 1 to 10 and the partial structures O-E-O are respectively Formula (23), Formula (23'), Formula (24) and Formula (24'):

Next, the production method of optically active titanium complexes of Formula (1), Formula (1'), Formula (2), Formula (2'), Formula (3), Formula (3'), Formula (4) and Formula (4') is described.

Salan ligands of the following Formula (26), Formula (26'), Formula (28) and Formula (28) which are ligands of titanium salan complexes of Formula (2), Formula (2'), Formula (4) and Formula (4') can be respectively produced by reducing salen compounds of the following Formula (25), Formula (25'), Formula (27) and Formula (27') respectively.

Examples of the reductant include sodium borohydride (NaBH$_4$), sodium borohydride cyanide (NaBH$_3$CN) and lithium aluminum hydride (LiAlH$_4$), and sodium borohydride (NaBH$_4$) is preferred.

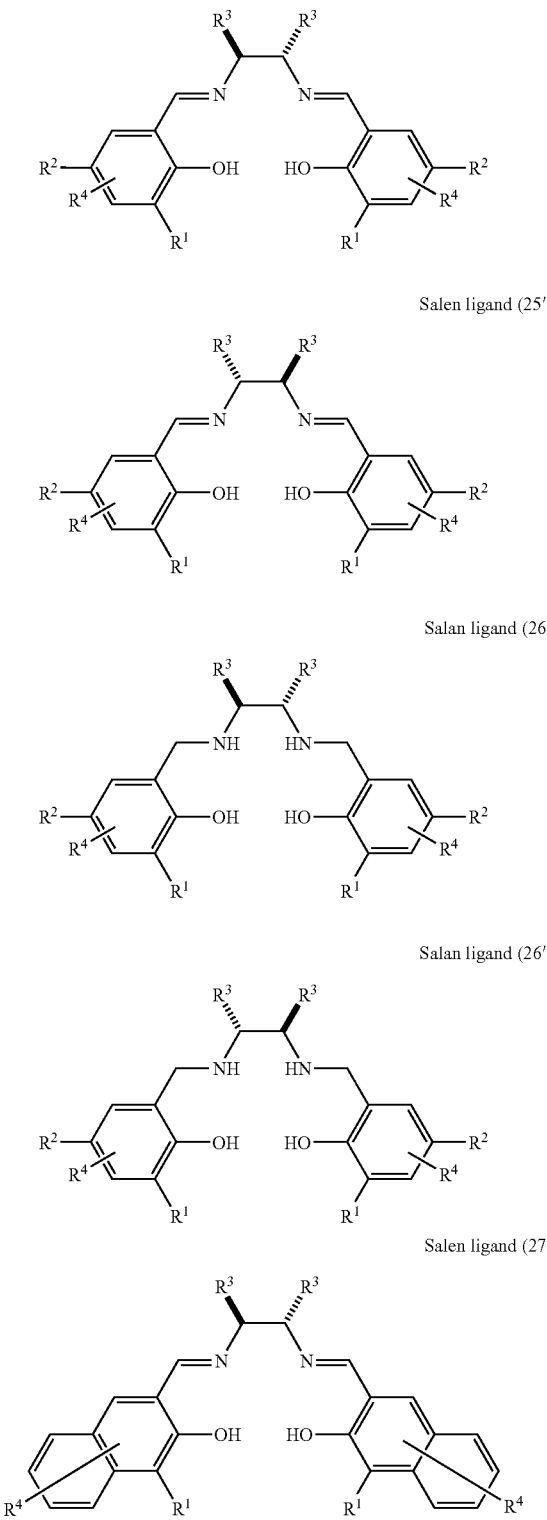

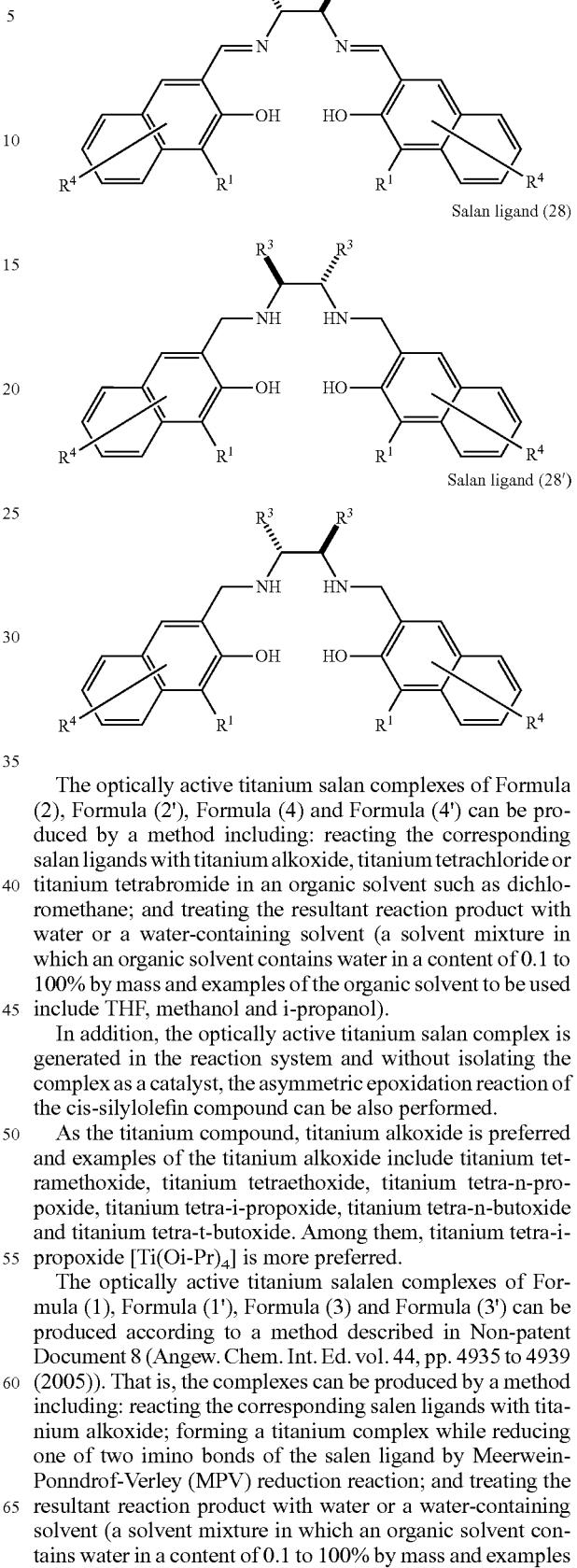

The optically active titanium salan complexes of Formula (2), Formula (2'), Formula (4) and Formula (4') can be produced by a method including: reacting the corresponding salan ligands with titanium alkoxide, titanium tetrachloride or titanium tetrabromide in an organic solvent such as dichloromethane; and treating the resultant reaction product with water or a water-containing solvent (a solvent mixture in which an organic solvent contains water in a content of 0.1 to 100% by mass and examples of the organic solvent to be used include THF, methanol and i-propanol).

In addition, the optically active titanium salan complex is generated in the reaction system and without isolating the complex as a catalyst, the asymmetric epoxidation reaction of the cis-silylolefin compound can be also performed.

As the titanium compound, titanium alkoxide is preferred and examples of the titanium alkoxide include titanium tetramethoxide, titanium tetraethoxide, titanium tetra-n-propoxide, titanium tetra-i-propoxide, titanium tetra-n-butoxide and titanium tetra-t-butoxide. Among them, titanium tetra-i-propoxide [Ti(Oi-Pr)$_4$] is more preferred.

The optically active titanium salalen complexes of Formula (1), Formula (1'), Formula (3) and Formula (3') can be produced according to a method described in Non-patent Document 8 (Angew. Chem. Int. Ed. vol. 44, pp. 4935 to 4939 (2005)). That is, the complexes can be produced by a method including: reacting the corresponding salen ligands with titanium alkoxide; forming a titanium complex while reducing one of two imino bonds of the salen ligand by Meerwein-Ponndrof-Verley (MPV) reduction reaction; and treating the resultant reaction product with water or a water-containing solvent (a solvent mixture in which an organic solvent contains water in a content of 0.1 to 100% by mass and examples of the organic solvent to be used include THF, methanol and i-propanol) after the completion of the above reaction.

In addition, the optically active titanium salalen complex is generated in the reaction system and without isolating the complex as a catalyst, the asymmetric epoxidation reaction of the cis-silylolefin compound can be also performed.

Here, examples of the titanium alkoxide include titanium tetramethoxide, titanium tetraethoxide, titanium tetra-n-propoxide, titanium tetra-i-propoxide, titanium tetra-n-butoxide and titanium tetra-t-butoxide. Among them, titanium tetra-i-propoxide [Ti(Oi-Pr)$_4$] is preferred. The amount of used titanium alkoxide is preferably in a range of 1 to 2 mol, relative to 1 mol of the salen ligand. In addition, the amount of used water is preferably in a range of 1 to 1,000 mol, more preferably in a range of 1 to 10 mol, relative to the equivalent of the salen ligand.

Examples of the reaction solvent for the production of the optically active titanium complex include aprotic organic solvents, protic organic solvents and a mixture of these solvents. Examples of the aprotic organic solvent include halogen-based solvents, aromatic hydrocarbon solvents, ester solvents, ether solvents and nitrile solvents and specific examples thereof include dichloromethane, chloroform, 1,2-dichloroethane, chlorobenzene, toluene, ethyl acetate, tetrahydrofitran, diethyl ether, butyronitrile, propionitrile and acetonitrile. Examples of the protic organic solvent include alcohol solvents and specific examples thereof include ethanol, i-propanol and t-butanol.

Preferred reaction solvents are aprotic organic solvents such as dichloromethane, 1,2-dichloroethane, chlorobenzene, toluene and ethyl acetate.

In the production method of the present invention, by subjecting a cis-silylolefin compound as a starting raw material to an asymmetric epoxidation using an optically active titanium complex of Formula (1), Formula (1'), Formula (2), Formula (2'), Formula (3), Formula (3') and Formula (4) and Formula (4'), one of the enantiomers of the cis-silylolefin oxide compound can be produced with a high selectivity ratio. Specifically, by using either the complex of Formula (1) or the complex of Formula (1'), one of both enantiomers of the optically active cis-silylolefin oxide compound can be selectively produced. By using either the complex of Formula (2) or the complex of Formula (2'), one of both enantiomers of the optically active cis-silylolefin oxide compound can be selectively produced. By using either the complex of Formula (3) or the complex of Formula (3'), one of both enantiomers of the optically active cis-silylolefin oxide compound can be selectively produced. By using either the complex of Formula (4) or the complex of Formula (4'), one of both enantiomers of the optically active cis-silylolefin oxide compound can be selectively produced.

Next, the production method of the optically active cis-silylolefin oxide compound of the present invention is described. This production method is a method for producing an optically active cis-silylolefin oxide compound of Formula (11):

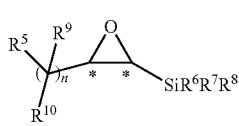

(11)

(where $R^5$, $R^6$, $R^7$, $R^8$, $R^9$, $R^{10}$ and n are the same as those defined above; and the absolute configuration of the carbon atom marked with "*" means (R) or (S)) by a method including: dissolving a cis-silylolefin compound of Formula (10):

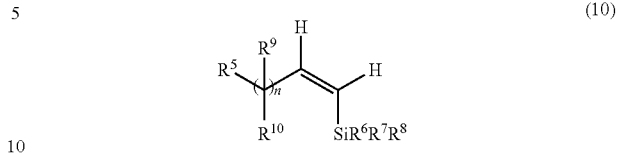

(10)

(where $R^5$, $R^6$, $R^7$, $R^8$, $R^9$, $R^{10}$ and n are the same as those defined above) and an optically active titanium complex of Formula (1), Formula (1'), Formula (2), Formula (2'), Formula (3), Formula (3'), Formula (4) and Formula (4') in an organic solvent in a nitrogen atmosphere or in the atmosphere; adding an oxidant into the resultant reaction solution; and stirring the resultant reaction mixture to effect the asymmetric epoxidation reaction, and the compound can be produced by a method shown in Reaction Formula 1:

Reaction Formula 1

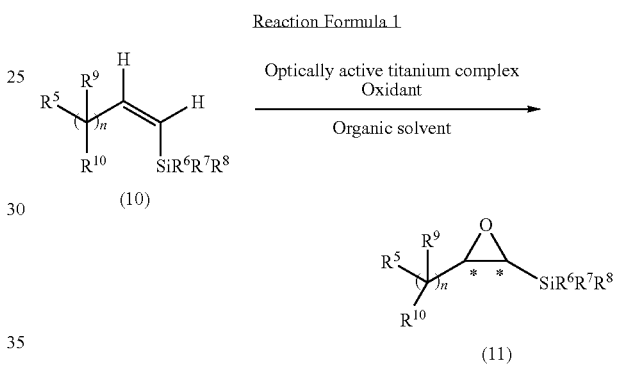

(where $R^5$, $R^6$, $R^7$, $R^8$, $R^9$, $R^{10}$ and n are the same as those defined above; and the absolute configuration of the carbon atom marked with "*" means (R) or (S)) shows a method for producing an optically active cis-silylolefin oxide compound of Formula (11) by treating a cis-silylolefin compound of Formula (10) with an oxidant and an optically active titanium complex in a solvent.

The cis-silylolefin compound of Formula (10) as the starting raw material of the present invent can be produced from a corresponding alkynyl silane and di-isobutyl aluminum hydride by a method described in Eisch, J. J.; Foxton, M. W. *J. Org. Chem.* vol. 36, p. 3520 (1971).

Each substituent of the cis-silylolefin compound of Formula (10) is specifically described.

$R^5$ in Formula (10) is a hydrogen atom, a $C_{1-22}$ alkyl group, a $C_{1-4}$ alkoxy group or a $C_{6-10}$ aryl group (the aryl group is unsubstituted or is substituted with a halogen atom, a $C_{1-4}$ alkyl group or a $C_{6-10}$ aryl group (the aryl group is unsubstituted or is substituted with a halogen atom, a $C_{1-4}$ alkyl group or a $C_{1-4}$ alkoxy group) or a $C_{1-4}$ alkoxy group).

$R^5$ is specifically described. Examples of $R^5$ as the $C_{1-22}$ alkyl group include a methyl group, an ethyl group, an n-propyl group, an i-propyl group, an n-butyl group, an i-butyl group; an s-butyl group, a t-butyl group, a pentyl group, an isopentyl group, a neopentyl group, a hexyl group, a heptyl group, an octyl group, a 2-ethylhexyl group, a nonyl group, a decyl group, an undecyl group, a dodecyl group, a tridecyl group, an isotridecyl group, a myristyl group, a palmityl group, a stearyl group, an icosyl group and a docosyl group. Examples of $R^5$ as the $C_{1-4}$ alkoxy group include a methoxy group, an ethoxy group, an n-propoxy group, an i-propoxy group, an n-butoxy group, an i-butoxy group, an s-butoxy group and a t-butoxy group. Examples of $R^5$ as the $C_{6-10}$ aryl group include a phenyl group, an o-fluorophenyl group, an m-fluorophenyl group, a p-fluorophenyl group, an o-chlorophenyl group, an m-chlorophenyl group, a p-chlorophenyl group, an o-bromophenyl group, an m-bromophenyl group, a p-bromophenyl group, an o-tolyl group, an m-tolyl group, a p-tolyl group, an o-ethylphenyl group, an m-ethylphenyl group, a p-ethylphenyl group, an o-(t-butyl)phenyl group, an m-(t-butyl)phenyl group, a p-(t-butyl)phenyl group, a 3,5-dimethylphenyl group, an o-methoxyphenyl group, an m-methoxyphenyl group, a p-methoxyphenyl group, an o-biphenylyl group, an m-biphenylyl group, a p-biphenylyl group, a 1-naphthyl group and a 2-naphthyl group.

$R^5$ is preferably a phenyl group, an o-fluorophenyl group, an m-fluorophenyl group, a p-fluorophenyl group, an o-chlorophenyl group, an m-chlorophenyl group, a p-chlorophenyl group, an o-bromophenyl group, an m-bromophenyl group, a p-bromophenyl group, an o-tolyl group, an m-tolyl group, a p-tolyl group, an o-ethylphenyl group, an m-ethylphenyl group, a p-ethylphenyl group, an o-(t-butyl)phenyl group, an m-(t-butyl)phenyl group, a p-(t-butyl)phenyl group, a 3,5-dimethylphenyl group, an o-methoxyphenyl group, an m-methoxyphenyl group, a p-methoxyphenyl group, an o-phenylphenyl group, an m-phenylphenyl group, a p-phenylphenyl group, a 1-naphthyl group or a 2-naphthyl group, and is preferably, for example a phenyl group, an o-bromophenyl group, an m-bromophenyl group, a p-bromophenyl group, an o-methoxyphenyl group, an m-methoxyphenyl group, a p-phenylphenyl group, a 1-naphthyl group or a 2-naphthyl group.

$R^6$, $R^7$ and $R^8$ in Formula (10) are each independently a halogen atom, a $C_{1-22}$ alkyl group or a $C_{6-10}$ aryl group (the aryl group is unsubstituted or is substituted with a halogen atom, a $C_{1-4}$ alkyl group or a $C_{1-4}$ alkoxy group).

$R^6$, $R^7$ and $R^8$ are specifically described. Examples of $R^6$, $R^7$ and $R^8$ as the $C_{1-22}$ alkyl group include a methyl group, an ethyl group, an n-propyl group, an i-propyl group, an n-butyl group, an i-butyl group, an s-butyl group, a t-butyl group, a pentyl group, an isopentyl group, a neopentyl group, a hexyl group, a heptyl group, an octyl group, a 2-ethylhexyl group, a nonyl group, a decyl group, an undecyl group, a dodecyl group, a tridecyl group, an isotridecyl group, a myristyl group, a palmityl group, a stearyl group, an icosyl group and a docosyl group. Examples of $R^6$, $R^7$ and $R^8$ as the $C_{6-10}$ aryl group include a phenyl group, an o-fluorophenyl group, an m-fluorophenyl group, a p-fluorophenyl group, an o-chlorophenyl group, an m-chlorophenyl group, a p-chlorophenyl group, an o-bromophenyl group, an m-bromophenyl group, a p-bromophenyl group, an o-tolyl group, an m-tolyl group, a p-tolyl group, an o-ethylphenyl group, an m-ethylphenyl group, a p-ethylphenyl group, an o-(t-butyl)phenyl group, an m-(t-butyl)phenyl group, a p-(t-butyl)phenyl group, a 3,5-dimethylphenyl group, an o-methoxyphenyl group, an m-methoxyphenyl group and a p-methoxyphenyl group.

Preferably, $R^6$, $R^7$ and $R^8$ are each independently a hydrogen atom, a methyl group, an ethyl group, an n-propyl group, an i-propyl group, an n-butyl group, an i-butyl group, an s-butyl group, a t-butyl group, a pentyl group, an isopentyl group, a neopentyl group, a hexyl group, a heptyl group, an octyl group, a 2-ethylhexyl group, a nonyl group, a decyl group, an undecyl group, a dodecyl group, a tridecyl group, an isotridecyl group, a myristyl group, a palmityl group, a stearyl group, an icosyl group, a docosyl group, a phenyl group, an o-fluorophenyl group, an m-fluorophenyl group, a p-fluorophenyl group, an o-chlorophenyl group, an m-chlorophenyl group, a p-chlorophenyl group, an o-bromophenyl group, an m-bromophenyl group, a p-bromophenyl group, an o-tolyl group, an m-tolyl group, a p-tolyl group, an o-ethylphenyl group, an m-ethylphenyl group, a p-ethylphenyl group, an o-(t-butyl)phenyl group, an m-(t-butyl)phenyl group, a p-(t-butyl)phenyl group, a 3,5-dimethylphenyl group, an o-methoxyphenyl group, an m-methoxyphenyl group or a p-methoxyphenyl group, and is more preferably, for example a methyl group or a phenyl group.

$R^9$ and $R^{10}$ in Formula (10) are each independently a hydrogen atom, a $C_{1-6}$ alkyl group (the alkyl group may be optionally substituted with a halogen atom, a $C_{1-6}$ alkoxy group (the alkoxy group may be optionally substituted with a halogen atom) or a hydroxy group) or a $C_{6-14}$ aryl group (the aryl group may be optionally substituted with a halogen atom, a hydroxy group, a nitro group, a cyano group, a $C_{1-6}$ alkyl group (the alkyl group may be optionally substituted with a halogen atom, a $C_{1-6}$ alkoxy group (the alkoxy group may be optionally substituted with a halogen atom) or a hydroxy group) or a $C_{1-6}$ alkoxy group (the alkoxy group may be optionally substituted with a halogen atom)).

Each substituent of $R^9$ and $R^{10}$ in Formula (10) is specifically described. Examples of $R^9$ and $R^{10}$ as the $C_{1-6}$ alkyl group include a methyl group, a trifluoro methyl group, an ethyl group, an n-propyl group, an i-propyl group, an n-butyl group, an i-butyl group, an s-butyl group, a t-butyl group, a 1-pentyl group, a 2-pentyl group, a 3-pentyl group, an i-pentyl group, a neopentyl group, a 2,2-dimethylpropyl group, a 1-hexyl group, a 2-hexyl group, a 3-hexyl group, a 1-methyl-n-pentyl group, a 1,1,2-trimethyl-n-propyl group, a 1,2,2-trimethyl-n-propyl group and a 3,3-dimethyl-n-butyl group; and as the $C_{6-14}$ aryl group include a phenyl group, an o-biphenylyl group, an m-biphenylyl group, a p-biphenylyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group and a 9-phenanthryl group.

$R^9$ and $R^{10}$ in Formula (10) are preferably a hydrogen atom, a methyl group, a trifluoromethyl group, an ethyl group or a phenyl group, and is more preferably a methyl group.

n in Formula (10) is an integer of 0 to 3.

An optically active titanium complex of any one of Formula (1), Formula (1'), Formula (2), Formula (2'), Formula (3), Formula (3'), Formula (4) and Formula (4') is used as a catalyst, and the amount of the used optically active titanium complex is in a range of 0.001 to 100 mol %, preferably in a range of 0.01 to 20 mol %, more preferably in a range of 0.3 to 5 mol %, based on the mol of the cis-silylolefin compound of Formula (10).

An optically active titanium complex of any one of Formula (1), Formula (1'), Formula (2), Formula (2'), Formula (3), Formula (3'), Formula (4) and Formula (4') is used as a catalyst, and examples of the solvent used for the asymmetric epoxidation reaction include: aprotic organic solvents such as halogen-based solvents, aromatic hydrocarbon solvents, ester solvents, ether solvents and nitrile solvents; and protic organic solvents such as alcohol solvents. Examples of the halogen-based solvent include dichloromethane, chloroform, 1,2-dichloroethane and chlorobenzene; examples of the aromatic hydrocarbon solvent include benzene and toluene; examples of the ester solvent include ethyl acetate; examples of the ether solvent include tetrahydrofuran and diethyl ether; and examples of the nitrile solvent include butyronitrile, propionitrile and acetonitrile. Examples of the alcohol solvent include methanol, ethanol, i-propanol, and further the above solvent mixture. In addition, when an aqueous solution of hydrogen peroxide (hydrogen peroxide water) is used in the present reaction, the aqueous solution is mixed with an organic solvent which does not dissolve in water, so that an organic phase and an aqueous phase may be separated from each other, however, such a two phase-solvent can be used as the reaction solvent of the present invention. Preferred examples of the solvent include aprotic organic solvents such as dichloromethane, 1,2-dichloroethane, chlorobenzene, toluene, ethyl acetate and a mixture of these solvents.

As the production operation, by adding a cis-silylolefin compound, an optically active titanium complex and an oxidant to an organic solvent, the reaction is progressed. As the adding order, it is preferred to add the oxidant to a solution containing the organic solvent, the cis-silylolefin compound and the optically active titanium complex.

Specific examples of the oxidant used in the reaction include iodosobenzene, sodium hypochlorite, m-chloro-perbenzoic acid, Oxone (registered trademark of E.I. du Pont de Nemours and Company), hydrogen peroxide water, urea-hydrogen peroxide adduct (UHP), oxaziridine, N-methylmorpholine oxide (NMO), t-butyl hydroperoxide (TBHP), cumyl hydroperoxide (CHP) and a mixture of these oxidants. Among them, hydrogen peroxide water, urea-hydrogen peroxide adduct (UHP) and a mixture of these oxidants are preferred. The concentration of the oxidant when the oxidant is hydrogen peroxide water is, for example in a range of 1 to 100% (% by weight), preferably in a range of 5 to 60% (% by weight).

The amount of the oxidant used in the reaction is, for example in a range of 1 to 10 equivalent(s), preferably in a range of 1 to 3 equivalent(s), based on the amount of the cis-silylolefin compound of Formula (10).

Examples of the adding method of the oxidant include a bulk adding, a fractional adding and a continuous adding.

In the case of the continuous adding, the adding rate is preferably in a range in which an internal temperature in the reaction solvent system is not rapidly elevated and specifically is preferably in a range of 0.01 to 40,000 equivalents per hour, more preferably in a range of 0.05 to 0.3 equivalents per hour. In addition, the fractional adding means that the oxidant to be used is divided into p doses (p is an arbitral integer) to be added. The division may be an aliquot or a non-aliquot and p is preferably in a range of 2 to 100.

Examples of the reaction temperature include a range of −78° C. to a solvent reflux temperature and a range of a melting temperature of the used solvent to a solvent reflux temperature, and the reaction temperature is preferably in a range of −20 to 50° C., more preferably in a range of 0 to 35° C.

Examples of the pressure in the reaction system include a range of 10 kPa to 1,100 kPa, and the pressure is preferably 15 kPa to 200 kPa. By pressurizing the reaction system, the reaction can be effected at a temperature higher than a solvent reflux temperature under normal pressure.

During the reaction, by additionally adding the optically active titanium complex as a catalyst, the reaction time can be reduced. In addition, by additionally adding the oxidant, the reaction time can be reduced.

After the completion of the reaction, by isolating-purifying the reaction product through an operation such as a distillation operation, silicagel column chromatography, a separation-extraction operation, a recrystallization operation and a combination of these operations, the objective optically active cis-silylolefin oxide compound can be obtained.

The optical purity of the obtained optically active cis-silylolefin oxide compound can be analyzed according to optically active high performance liquid chromatography analysis, optically active gas chromatography analysis, optical rotation measurement, or the like.

The optically active cis-silylolefin oxide compound obtained by the production method of the present invention can be derived to various compounds as follows:

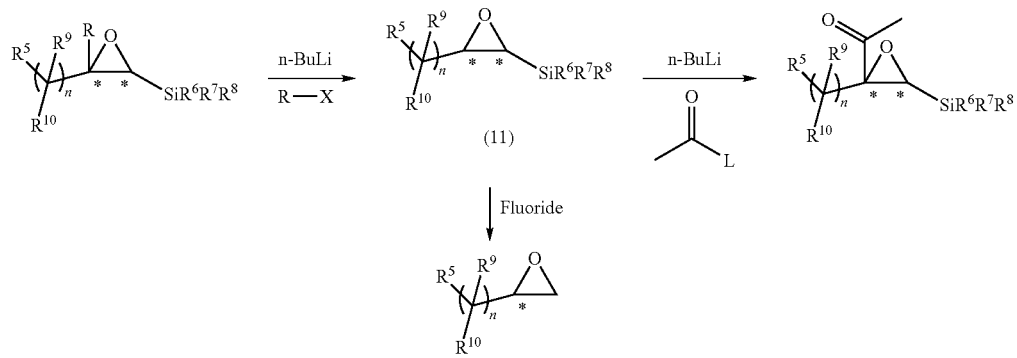

(where $R^5$, $R^6$, $R^7$, $R^8$, $R^9$, $R^{10}$ and n are the same as those defined above; the absolute configuration of the carbon atom marked with "*" means (R) or (S); R is an alkyl group or the like; X is a chlorine atom, a bromine atom, an iodine atom or the like; and L is a leaving group such as a methoxy(methyl)amino group).

Hereinafter, the present invention will be described more in detail referring to Examples which should not be construed as limiting the scope of the present invention.

Here, in the following Examples, all reactions were effected in a glass container heat-dried beforehand while stirring the reaction mixture with a stirring rod. $^1$H NMR spectrum and $^{13}$C NMR spectrum were measured using JEOL AL-400 spectrometer. In $^1$H NMR, tetramethylsilane (TMS) was used as the internal standard substance (0 ppm) and in $^{13}$C NMR, CDCl$_3$ was used as the internal standard substance (77.0 ppm). The optical rotation was measured using JASCO P-1020 polarimeter. HPLC (high performance liquid chromatography) was measured using Shimazu LC-10AT-VP in which a detector for various wavelengths is fitted to an optically active column (manufactured by Daicel Chemical Industries, Ltd.). As methylene chloride and hydrogen peroxide water (30 to 35% in water), those purchased from Kanto Chemical Co., Inc. as they were, were used. (Z)-alkenylsilane was synthesized from a corresponding alkynylsilane by a method described in Eisch, J. J.; Foxton, M. W. *J. Org. Chem.* vol. 36, p. 3520 (1971).

EXAMPLES

Example 1

Asymmetric Oxidation of Alkenylsilane

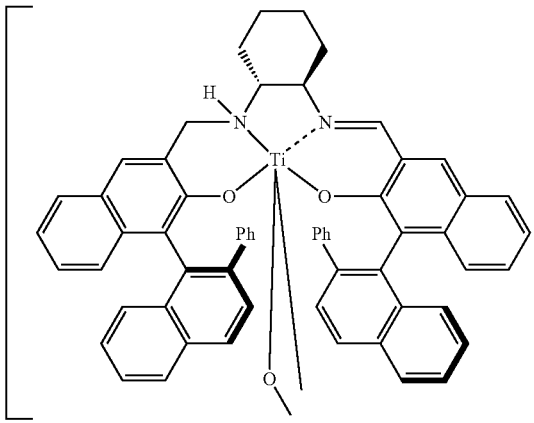

A titanium salalen complex 1 (4.5 to 18 mg, 0.5 to 2.0 mol %) of the above formula and alkenylsilane (0.50 mmol) were dissolved in $CH_2Cl_2$ (0.50 mL) and thereto, 30 to 35% hydrogen peroxide water (85 μL, 0.75 mmol) was added, followed by stirring the resultant reaction mixture at 25° C. After the completion of the reaction, the mixture was purified by silica gel column chromatography using n-pentane as a developing solvent to produce the objective epoxysilane. The optical purity (ee) thereof was determined by an optically active HPLC analysis.

Example 2

Production of Styrene Oxide from Epoxysilane

The epoxysilane was dissolved in THF (4 mL/mmol). Thereto, tetrabutylammonium fluoride (TBAF) (1 $molL^{-1}$ THF solution, 1.5 to 2 equivalents) was added and the resultant reaction mixture was stirred at a room temperature or 50° C. After the completion of the reaction, the mixture was extracted with diethyl ether and the extract was washed with water and saline and dried over $Na_2SO_4$. The crude product was purified by silica gel chromatography using n-pentane/diethyl ether as a developing solvent to produce a corresponding epoxide. The optical purity (ee) thereof was determined by an optically active HPLC analysis.

Hereinafter, the yield, the optical purity and the physical properties of the compound produced according to Examples 1 and 2 are shown. In addition, CHIRALPAK IC, CHIRALCEL OD-H, CHIRALPAK AD-H, CHIRALPAK IA and CHIRALCEL OJ-H which were used for the determination of the optical purity are registered trademarks of Daicel Chemical Industries, Ltd.

Trimethyl((2R,3S)-3-phenyloxirane-2-yl) silane

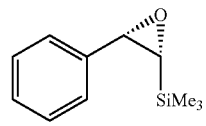

Colorless oily substance, 87% yield, >99% ee (CHIRALPAK IC, hexane/iPrOH 99.9:0.1); $[\alpha]D^{25}$ +64.7° (c=0.77, $CHCl_3$); FTIR (neat): n=3061, 3030, 2955, 2903, 1607, 1499, 1450, 1389, 1315, 1252, 1188, 1072, 1026, 905, 845, 737, 700, 648 $cm^{-1}$; $^1H$ NMR ($CDCl_3$): δ7.35-7.23 (m, 5H), 4.26-4.25 (d, J=5.4 Hz, 1H), 2.52-2.51 (d, J=5.4 Hz, 1H), −0.17 ppm (s, 9H); $^{13}C$ NMR ($CDCl_3$): δ138.0, 128.0, 127.4, 126.1, 57.1, 53.4, −2.3 ppm; Element analysis: calculated values of $C_{11}H_{16}OSi$ (%): C, 68.69; H, 8.39; measured values: C, 68.83; H, 8.42.

(S)-2-phenyloxirane

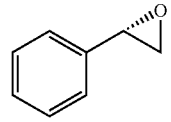

Colorless oily substance, 69% yield, >99% ee (CHIRALCEL OD-H, hexane/iPrOH 99.9:0.1); $[\alpha]D^{23}$ +26.1° (c=0.48, $CHCl_3$); $^1H$ NMR ($CDCl_3$): δ7.39-7.26 (m, 5H), 3.88-3.85 (dd, J=2.6, 4.0 Hz, 1H), 3.17-3.13 (dd, J=4.0, 5.6 Hz, 1H), 2.82-2.79 ppm (dd, J=2.6, 5.6 Hz, 1H).

Dimethyl(phenyl) ((2R,3S)-3-phenyloxirane-2-yl) silane

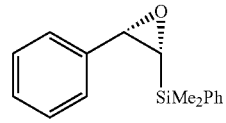

Colorless oily substance, 95% yield, >99% ee (CHIRALPAK AD-H, hexane/iPrOH 99.9:0.1); $[\alpha]D^{24}$ +33.9° (c=0.79, $CHCl_3$); FTIR (neat): n=3059, 3034, 2957, 2905, 1595, 1489, 1455, 1423, 1389, 1312, 1252, 1184, 1113, 1072, 1026, 903, 822, 777, 733, 700, 667 $cm^{-1}$; $^1H$ NMR ($CDCl_3$): δ7.42-7.24 (m, 10H), 4.29-4.27 (d, J=5.3 Hz, 1H), 2.72-2.70 (d, J=5.3 Hz, 1H), 0.08 (s, 3H), −0.04 ppm (s, 3H); $^{13}C$ NMR ($CDCl_3$): δ137.5, 136.9, 133.8, 129.3, 127.9, 127.8, 127.4, 126.2, 57.1, 52.9, −3.4, −4.2 ppm; Element analysis: calculated values of $C_{16}H_{18}OSi$ (%): C, 75.54; H, 7.13; measured values: C, 75.43; H, 7.15.

[(2R,3S)-3-(2-methoxyphenyl) oxirane-2-yl]trimethylsilane

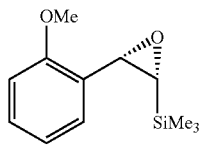

Colorless oily substance, 94% yield, >99% ee (CHIRALCEL OD-H, hexane/iPrOH 99.9:0.1); [α]D$^{24}$ +153° (c=0.78, CHCl$_3$); FTIR (neat): n=3045, 2955, 2905, 2837, 1597, 1495, 1462, 1387, 1313, 1250, 1171, 1111, 1028, 905, 841, 754, 718, 652 cm$^{-1}$; $^1$H NMR (CDCl$_3$): δ7.30-7.22 (m, 2H), 6.93-6.89 (m, 1H), 6.84-6.82 (d, J=8.3 Hz, 1H), 4.23-4.22 (d, J=5.4 Hz, 1H), 3.85 (s, 3H), 2.59-2.57 (d, J=5.4 Hz, 1H), −0.20 ppm (s, 9H); $^{13}$C NMR (CDCl$_3$): δ157.6, 128.4, 126.9, 126.7, 120.0, 109.3, 55.0, 54.4, 53.1, −2.4 ppm; Element analysis: calculated values of C$_{12}$H$_{18}$O$_2$Si (%): C, 64.82; H, 8.16; measured values: C, 65.01; H, 8.20.

(S)-2-(2-methoxyphenyl) oxirane

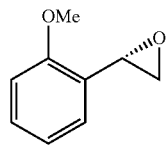

Colorless oily substance, 81% yield, >99% ee (CHIRALPAK IC, hexane/iPrOH 99.9:0.1); [α]D$^{24}$ +55.3° (c=0.93, CHCl$_3$); FTIR (neat): n=3047, 2993, 2947, 2839, 1597, 1497, 1464, 1387, 1288, 1250, 1169, 1134, 1101, 1026, 989, 937, 881, 822, 799, 754 cm$^{-1}$; $^1$H NMR (CDCl$_3$): δ7.30-7.23 (m, 1H), 7.17-7.13 (dd, J=2.0, 7.6 Hz, 1H), 6.97-6.91 (ddd, J=0.7, 7.6, 8.2 Hz, 1H), 6.90-6.87 (dd, J=0.7, 8.2 Hz, 1H), 4.22-4.19 (dd, J=2.6, 4.3 Hz, 1H), 3.87 (s, 3H), 3.16-3.12 (dd, J=4.3, 5.6 Hz, 1H), 2.72-2.69 ppm (dd, J=2.6, 5.6 Hz, 1H); $^{13}$C NMR (CDCl$_3$): δ158.1, 128.8, 126.1, 125.0, 120.7, 110.1, 55.4, 50.6, 48.2 ppm; Element analysis: calculated values of C$_{12}$H$_{18}$O$_2$Si (%): C, 64.82; H, 8.16; measured values: C, 65.01; H, 8.20.

[(2R,3S)-3-(3-methoxyphenyl) oxirane-2-yl]trimethylsilane

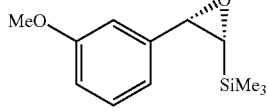

Colorless oily substance, 96% yield, >99% ee (CHIRALCEL OD-H, hexane/iPrOH 99.9:0.1); [α]D$^{24}$ +44.9° (c=0.91, CHCl$_3$); FTIR (neat): n=3055, 2955, 2905, 2837, 1595, 1487, 1460, 1431, 1385, 1319, 1283, 1244, 1155, 1043, 897, 845, 783, 762, 729, 696 cm$^{-1}$; $^1$H NMR (CDCl$_3$): δ7.25-7.19 (dd, J=7.9, 7.9 Hz, 1H), 6.94-6.89 (m, 2H), 6.82-6.78 (m, 1H), 4.24-4.22 (d, J=5.6 Hz, 1H), 3.80 (s, 3H), 2.52-2.50 (d, J=5.64 Hz, 1H), −0.15 ppm (s, 9H); $^{13}$C NMR (CDCl$_3$): δ159.4, 139.6, 129.1, 118.6, 113.3, 111.3, 57.0, 55.2, 53.5, −2.2 ppm; Element analysis: calculated values of C$_{12}$H$_{18}$O$_2$Si (%): C, 64.82; H, 8.16; measured values: C, 64.94; H, 8.19.

(s)-2-(3-methoxyphenyl) oxirane

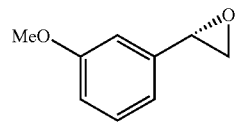

Colorless oily substance, 85% yield, >99% ee (CHIRALPAK IC, hexane/iPrOH 99.9:0.1); [α]D$^{24}$ +12.6° (c=0.88, CHCl$_3$); $^1$H NMR (CDCl$_3$): δ7.28-7.24 (m, 1H), 6.90-6.81 (m, 3H), 3.85-3.84 (m, 1H), 3.81 (s, 3H), 3.15-3.12 (m, 1H), 2.79-2.77 ppm (ddd, J=1.2, 2.4, 5.6 Hz, 1H).

[(2R,3S)-3-(2-bromophenyl) oxirane-2-yl]trimethylsilane

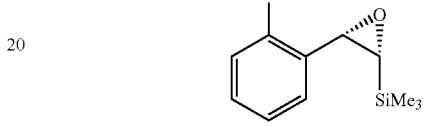

Colorless oily substance, 10% yield, >99% ee (CHIRALPAK IC, hexane/iPrOH 99.9:0.1); [α]D$^{24}$ +148.2° (c=0.91, CHCl$_3$); FTIR (neat): n=3063, 2957, 2907, 2860, 1572, 1470, 1435, 1414, 1383, 1315, 1250, 1190, 1155, 1115, 1053, 1024, 910, 847, 750, 696, 660 cm$^{-1}$; $^1$H NMR (CDCl$_3$): δ7.53-7.50 (dd, J=1.0, 7.9 Hz, 1H), 7.39-7.36 (dd, J=1.6, 7.6 Hz, 1H), 7.31-7.25 (m, 1H), 7.19-7.12 (m, 1H), 4.22-4.20 (d, J=5.3 Hz, 1H), 2.65-2.63 (d, J=5.3 Hz, 1H), −0.16 ppm (s, 9H); $^{13}$C NMR (CDCl$_3$): δ137.8, 131.8, 129.0, 128.1, 127.0, 122.5, 58.1, 53.7, −2.3 ppm; Element analysis: calculated values of C$_{11}$H$_{15}$BrOSi (%): C, 48.71; H, 5.57; measured values: C, 48.92; H, 5.58.

(S)-2-(2-bromophenyl) oxirane

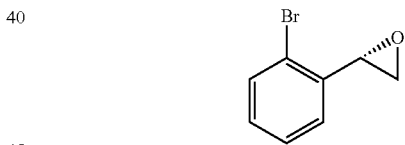

Colorless oily substance, 82% yield, >99% ee (CHIRALPAK IC, hexane/iPrOH 99.9:0.1); [α]D$^{24}$ +54.6° (c=0.65, CHCl$_3$); $^1$H NMR (CDCl$_3$): δ7.55-7.53 (dd, J=1.0, 8.1 Hz, 1H), 7.33-7.29 (m, 1H), 7.24-7.22 (dd, J=2.0, 7.6 Hz, 1H), 7.19-7.15 (m, 1H), 4.17-4.14 (dd, J=2.7, 4.2 Hz, 1H), 3.20-3.18 (dd, J=4.2, 5.6 Hz, 1H), 2.66-2.64 ppm (dd, J=2.7, 5.6 Hz, 1H).

[(2R,3S)-3-(3-bromophenyl) oxirane-2-yl]trimethylsilane

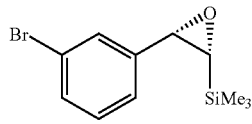

Colorless oily substance, 98% yield, >99% ee (CHIRALCEL OJ-H, hexane/iPrOH 99.9:0.1); [α]D$^{24}$ +28.1° (c=1.00, CHCl$_3$); FTIR (neat): n=3063, 2957, 2903, 2799, 1597, 1568, 1516, 1474, 1420, 1379, 1252, 1186, 1069, 1040, 999, 907, 841, 762, 700 cm$^{-1}$; $^1$H NMR (CDCl$_3$): δ7.50-7.49 (m, 1H), 7.42-7.38 (m, 1H), 7.29-7.26 (m, 1H), 7.21-7.16 (dd, J=7.6, 7.6 Hz, 1H), 4.21-4.19 (d, J=5.3 Hz, 1H), 2.53-2.51 (d, J=5.3 Hz, 1H), −0.14 ppm (s, 9H); $^{13}$C NMR (CDCl$_3$): δ140.4, 130.5, 129.6, 129.2, 124.8, 122.2, 56.4, 53.7, −2.2 ppm; Element analysis: calculated values of C$_{11}$H$_{15}$BrOSi (%): C, 48.71; H, 5.57; measured values: C, 48.87; H, 5.61.

(S)-2-(3-bromophenyl) oxirane

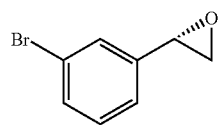

Colorless oily substance, 79% yield, >99% ee (CHIRAL-PAK IC, hexane/iPrOH 99.9:0.1); [α]D$^{24}$ +9.0° (c=1.20, CHCl$_3$); $^1$H NMR (CDCl$_3$): δ7.45-7.42 (m, 2H), 7.23-7.21 (m, 2H), 3.84-3.81 (dd, J=2.6, 4.0 Hz, 1H), 3.16-3.13 (dd, J=4.0, 5.6 Hz, 1H), 2.77-2.74 ppm (dd, J=2.6, 5.6 Hz, 1H).

[(2R,3S)-3-(4-bromophenyl) oxirane-2-yl]trimethylsilane

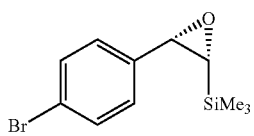

Colorless oily substance, 91% yield, >99% ee (CHIRAL-PAK IC, hexane/iPrOH 99.9:0.1); [α]D$^{25}$ +49.6° (c=1.06, CHCl$_3$); FTIR (neat): n=3036, 2957, 2903, 1595, 1487, 1404, 1252, 1184, 1099, 1069, 1011, 907, 843, 752, 704, 658 cm$^{-1}$; $^1$H NMR (CDCl$_3$): δ7.47-7.43 (m, 2H), 7.24-7.20 (m, 2H), 4.19-4.17 (d, J=5.4 Hz, 1H), 2.52-2.51 (d, J=5.4 Hz, 1H), −0.16 ppm (s, 9H); $^{13}$C NMR (CDCl$_3$): δ137.1, 131.1, 127.9, 121.2, 56.6, 53.6, −2.2 ppm; Element analysis: calculated values of C$_{11}$H$_{15}$BrOSi (%): C, 48.71; H, 5.57; measured values: C, 48.91; H, 5.62.

(S)-2-(4-bromophenyl) oxirane

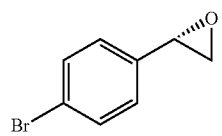

Colorless oily substance, 82% yield, >99% ee (CHIRAL-PAK IC, hexane/iPrOH 99.9:0.1); [α]D$^{24}$ +20.5° (c=1.27, CHCl$_3$); $^1$H NMR (CDCl$_3$): δ 7.50-7.45 (m, 2H), 7.18-7.13 (m, 2H), 3.84-3.81 (dd, J=2.6, 4.0 Hz, 1H), 3.16-3.13 (dd, J=4.0, 5.6 Hz, 1H), 2.77-2.74 ppm (dd, J=2.6, 5.6 Hz, 1H).

[(2R,3S)-3-(biphenyl-4-yl) oxirane-2-yl]trimethylsilane

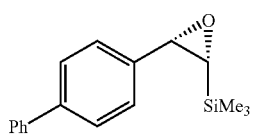

White solid, 99% yield, >99% ee (CHIRALPAK AD-H, hexane/iPrOH 99.9:0.1); $^1$H NMR (CDCl$_3$): δ7.62-7.55 (m, 4H), 7.46-7.31 (m, 5H), 4.30-4.28 (d, J=5.3 Hz, 1H), 2.56-2.54 (d, J=5.3 Hz, 1H), −0.14 ppm (s, 9H); $^{13}$C NMR (CDCl$_3$): δ140.7, 140.3, 137.1, 128.8, 127.3, 127.0, 126.7, 126.6, 56.9, 53.6, −2.2 ppm; Element analysis: calculated values of C$_{11}$H$_{15}$BrOSi (%): C, 48.71; H, 5.57; measured values: C, 48.91; H, 5.62.

(S)-2-(biphenyl-4-yl) oxirane

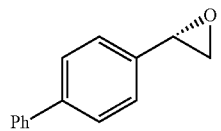

White solid, 90% yield, >99% ee (CHIRALPAK IC, hexane/iPrOH 99.9:0.1); [α]D$^{22}$ +28.3° (c=1.05, CHCl$_3$); $^1$H NMR (CDCl$_3$): δ7.60-7.57 (m, 4H), 7.47-7.41 (m, 2H), 7.37-7.34 (m, 3H), 3.93-3.90 (dd, J=2.6, 4.0 Hz, 1H), 3.20-3.17 (dd, J=4.0, 5.6 Hz, 1H), 2.87-2.84 ppm (dd, J=2.6, 5.6 Hz, 1H).

Trimethyl[(2R,3S)-3-(naphthalene-1-yl) oxirane-2-yl]silane

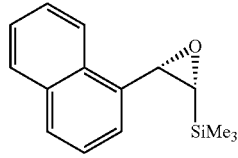

Colorless oily substance, 92% yield, >99% ee (CHIRAL-CEL OD-H, hexane/iPrOH 99.9:0.1); [α]D$^{24}$ +258.8° (c=0.88, CHCl$_3$); FTIR (neat): n=3053, 2953, 2901, 1593, 1510, 1412, 1371, 1342, 1252, 1213, 1157, 1059, 1024, 910, 843, 785, 696, 642 cm$^{-1}$; $^1$H NMR (CDCl$_3$): δ8.08-8.05 (m, 1H), 7.89-7.86 (m, 1H), 7.79-7.77 (d, J=8.5 Hz, 1H), 7.57-7.49 (m, 3H), 7.45-7.41 (dd, J=7.3, 8.1 Hz, 1H), 4.66-4.65 (d, J=5.4 Hz, 1H), 2.79-2.77 (d, J=5.4 Hz, 1H), −0.33 ppm (s, 9H); $^{13}$C NMR (CDCl$_3$): δ133.9, 133.0, 131.2, 128.6, 127.7, 126.0, 125.8, 125.2, 123.5, 123.3, 56.1, 53.5, −2.4 ppm; Element analysis: calculated values of C$_{15}$H$_{18}$OSi (%): C, 74.33; H, 7.49; measured values: C, 74.42; H, 7.59.

(S)-2-(naphthalene-1-yl) oxirane

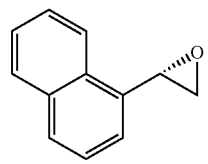

Colorless oily substance, 93% yield, >99% ee (CHIRAL-PAK IC, hexane/iPrOH 99.9:0.1); [α]D$^{24}$ +88.8° (c=0.83, CHCl$_3$); $^1$H NMR (CDCl$_3$): δ8.16-8.14 (m, 1H), 7.91-7.88 (m, 1H), 7.82-7.80 (m, 1H), 7.59-7.44 (m, 4H), 4.51-4.49 (dd, J=2.9, 4.2 Hz, 1H), 3.32-3.29 (dd, J=4.2, 5.9 Hz, 1H), 2.83-2.81 ppm (dd, J=2.9, 5.9 Hz, 1H).

Trimethyl[(2R,3S)-3-(naphthalene-2-yl) oxirane-2-yl]silane

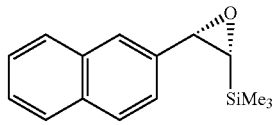

Colorless oily substance, 96% yield, >99% ee (CHIRALPAK IA, hexane/iPrOH 99.9:0.1); [α]$_D^{24}$ −4.7° (c=0.74, CHCl$_3$); FTIR (neat): n=3053, 2955, 2903, 1603, 1508, 1393, 1348, 1250, 1157, 1128, 1026, 893, 845, 795, 752, 700 cm$^{-1}$; $^1$H NMR (CDCl$_3$): δ7.84-7.79 (m, 4H), 7.50-7.45 (m, 3H), 4.40-4.39 (d, J=5.4 Hz, 1H), 2.61-2.60 (d, J=5.4 Hz, 1H), −0.18 ppm (s, 9H); $^{13}$C NMR (CDCl$_3$): δ 135.5, 133.0, 132.8, 127.8, 127.7, 127.7, 126.2, 125.8, 124.7, 124.3, 57.3, 53.8, −2.1 ppm; Element analysis: calculated values of C$_{15}$H$_{18}$OSi (%): C, 74.33; H, 7.49; measured values: C, 74.11; H, 7.59.

(S)-2-(naphthalene-2-yl) oxirane

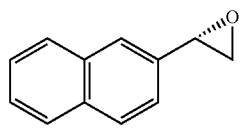

Colorless oily substance, 93% yield, >99% ee (CHIRALPAK IC, hexane/iPrOH 99.9:0.1); [α]$_D^{24}$ +12.4° (c=0.90, CHCl$_3$); $^1$H NMR (CDCl$_3$): δ7.84-7.80 (m, 4H), 7.52-7.44 (m, 2H), 7.35-7.31 (dd, J=1.6, 8.6 Hz, 1H), 4.05-4.02 (dd, J=2.6, 4.0 Hz, 1H), 3.25-3.21 (dd, J=4.0, 5.6 Hz, 1H), 2.93-2.90 ppm (dd, J=2.6, 5.6 Hz, 1H).

Trimethyl[(2R,3S)-3-phenethyloxirane-2-yl]silane

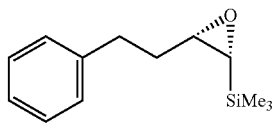

Colorless oily substance, 12% yield, 97% ee (CHIRALCEL OD-H, hexane/iPrOH 99.9:0.1); [α]$_D^{25}$ +3.1° (c=0.82, CHCl$_3$); FTIR (neat): n=3061, 3026, 2957, 2924, 2858, 1599, 1495, 1452, 1418, 1329, 1252, 1180, 1070, 1028, 953, 843, 750, 698 cm$^{-1}$; $^1$H NMR (CDCl$_3$): δ7.32-7.28 (m, 2H), 7.22-7.19 (m, 3H), 3.17-3.13 (m, 1H), 2.91-2.83 (m, 1H), 2.80-2.73 (m, 1H), 2.24-2.22 (d, J=5.2 Hz, 1H), 1.93-1.85 (m, 1H), 1.80-1.71 (m, 1H), 0.13 ppm (s, 9H); $^{13}$C NMR (CDCl$_3$): δ141.4, 128.5, 128.4, 126.0, 57.0, 50.9, 33.5, 33.3, −1.7 ppm; Element analysis: calculated values of C$_{13}$H$_{20}$OSi (%): C, 70.85; H, 9.15; measured values: C, 70.68; H, 9.11.

(S)-2-phenethyloxirane

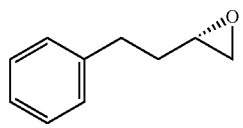

Colorless oily substance, 74% yield, 97% ee (CHIRALPAK IC, hexane/iPrOH 99.9:0.1); [α]$_D^{22}$ −16.3° (c=0.38, CHCl$_3$)): δ7.32-7.28 (m, 2H), 7.22-7.18 (m, 3H), 2.98-2.93 (m, 1H), 2.87-2.72 (m, 3H), 2.49-2.47 (dd, J=2.7, 5.1 Hz, 1H), 1.93-1.79 ppm (m, 2H).

Example 3

Asymmetric Oxidation of Alkenylsilane No. 2

To a dichloromethane solution (0.5 mL) of a salan ligand (27 mg, 0.050 mmol) (10 mol % based on the mol of the substrate) of Formula 2:

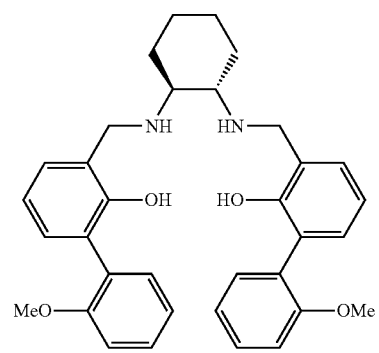

titanium tetraisopropoxide [Ti (Oi-Pr)$_4$] (2.8 mg, 0.010 mmol) was added at 20° C. The resultant reaction mixture was stirred at 20° C. for 1 hour and to the reaction mixture, a CH$_2$Cl$_2$ (0.50 mL) solution of cis-1-dimethyl(phenyl) silyl-2-phenylethylene (0.50 mmol) was added, followed by adding 30 to 35% hydrogen peroxide water (85 μL, 0.75 mmol) and by stirring the resultant reaction mixture at 40° C. After the completion of the reaction, the mixture was purified by silica gel column chromatography using n-pentane as a developing solvent to produce the objective dimethyl(phenyl) ((2R,3S)-3-phenyloxirane-2-yl]silane. The yield and the optical purity (ee) were 59% and 99% ee respectively.

Example 4

Production of trimethyl[(2R,3S)-3-methyl-3-(naphthalene-2-yl) oxirane-2-yl]silane Trimethyl[(2R,3S)-3-(naphthalene-2-yl) oxirane-2-yl]silane (9.8 μg, 0.40 mmol) was dissolved in THF anhydride (1.6 mL) in a nitrogen atmosphere and the resultant solution was cooled down to −78° C. Thereinto, n-butyl lithium (2.69 molL$^{-1}$ in 180.3 μL, 0.48 mmol of hexane solution) was dropped and the resultant reaction mixture was stirred at −78° C. for 90 minutes. Thereto, methyl iodide (99.8 μL, 1.60 mmol) was added and the resultant reaction mixture was stirred at −78° C. for 15 minutes. Thereafter, the reaction mixture was returned to the room temperature and was further stirred for 1 hour. The reaction was quenched with water and the resultant mixture was extracted with ethyl acetate. The organic phase was washed with water and saline and was dried over Na$_2$SO$_4$. The obtained crude product was purified by silica gel column chromatography (n-pentane/diethyl ether=0/0) to produce trimethyl [(2R,3S)-3-methyl-3-(naphthalene-2-yl) oxirane-2-yl]silane in a yield of 71%. Trimethyl [(2R,3S)-3-methyl-3-(naphthalene-2-yl) oxirane-2-yl]silane

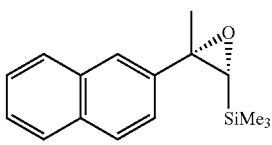

Colorless oily substance, 71% yield, >99% ee (CHIRAL-PAK IA, hexane/iPrOH 99.9:0.1); [α]$_D^{22}$ +9.4° (c=1.14, CHCl$_3$); FTIR (neat): n=3053, 3022, 2961, 2897, 1631, 1613, 1576, 1504, 1441, 1410, 1366, 1308, 1250, 1221, 1194, 1134, 1074, 1022, 955, 845, 777, 748, 671 cm$^{-1}$; $^1$H NMR (CDCl$_3$): δ 7.83-7.78 (m, 4H), 7.49-7.45 (m, 3H), 2.49 (s, 1H), 1.77 (s, 3H), −0.26 ppm (s, 9H); $^{13}$C NMR (CDCl$_3$): δ139.1, 133.0, 132.6, 127.9, 127.7, 127.6, 126.2, 125.8, 124.8, 124.8, 62.9, 61.0, 27.1, −2.5 ppm; Element analysis: calculated values of C$_{16}$H$_{20}$OSi (%): C, 74.95; H, 7.86; measured values: C, 75.07; H, 7.87.

This compound was derived to the following compound by a method described in Example 2.

(S)-2-methyl-2-(naphthalene-2-yl) oxirane

White solid, 85% yield, >99% ee (CHIRALCEL OJ-H, hexane/iPrOH 99.5:0.5); [α]$_D^{23}$ +3.3° (c=1.00, CHCl$_3$); $^1$H NMR (CDCl$_3$): δ7.85-7.80 (m, 4H), 7.51-7.43 (m, 3H), 3.06-3.04 (d, J=5.6 Hz, 1H), 2.90-2.88 ppm (d, J=5.6 Hz, 1H), 1.82 ppm (s, 3H).

INDUSTRIAL APPLICABILITY

According to the present invention, without using a separation operation for optically resolving the objective substance, an optically active cis-silylolefin oxide compound having a high optical purity of 99% ee or more can be obtained in a high yield of 90% or more and can be fully used as an intermediate for various compounds. Therefore, the present invention is industrially useful.

The invention claimed is:

1. A production method of an optically active cis-silylolefin oxide compound of Formula (11):

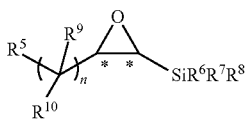

(11)

(where R$^5$ is a hydrogen atom, a C$_{1-22}$ alkyl group, a C$_{1-4}$ alkoxy group, or a C$_{6-10}$ aryl group (the aryl group is unsubstituted or is substituted with a halogen atom, a C$_{1-4}$ alkyl group, a C$_{6-10}$ aryl group (the aryl group is unsubstituted or is substituted with a halogen atom, a C$_{1-4}$ alkyl group or a C$_{1-4}$ alkoxy group) or a C$_{1-4}$ alkoxy group), R$^6$, R$^7$ and R$^8$ are each independently a hydrogen atom, a C$_{1-22}$ alkyl group or a C$_{6-10}$ aryl group (the aryl group is unsubstituted or is substituted with a halogen atom, a C$_{1-4}$ alkyl group or a C$_{1-4}$ alkoxy group), R$^9$ and R$^{10}$ are each independently a hydrogen atom, a C$_{1-6}$ alkyl group (the alkyl group is optionally substituted with a halogen atom, a C$_{1-6}$ alkoxy group (the alkoxy aryl group group is optionally substituted with a halogen atom) or a hydroxy group) or a C$_{6-14}$ (the aryl group is optionally substituted with a halogen atom, a hydroxy group, a nitro group, a cyano group, a C$_{1-6}$ alkyl group (the alkyl group is optionally substituted with a halogen atom, a C$_{1-6}$ alkoxy group (the alkoxy group is optionally substituted with a halogen atom) or a hydroxy group) or a C$_{1-6}$ alkoxy group (the alkoxy group is optionally substituted with a halogen atom)), n is an integer of 0 to 3, and the absolute configuration of the carbon atoms marked with "*" means (R) or (S)), characterized by subjecting a cis-silylolefin compound of Formula (10):

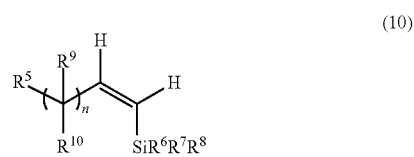

(10)

(where R$^5$, R$^6$, R$^7$, R$^8$, R$^9$, R$^{10}$ and n are the same as those defined above) to an asymmetric epoxidation with an oxidant using as a catalyst, an optically active titanium complex of any one of Formula (1), Formula (1'), Formula (2), Formula (2'), Formula (3), Formula (3'), Formula (4) and Formula (4'):

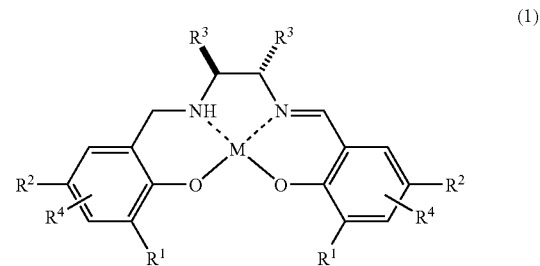

(1)

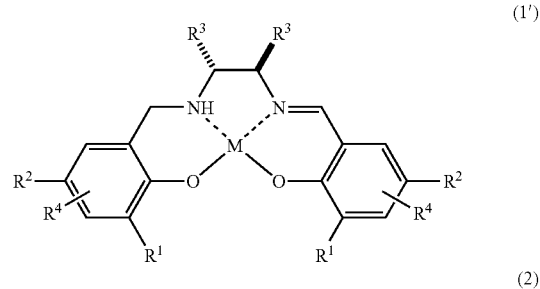

(1')

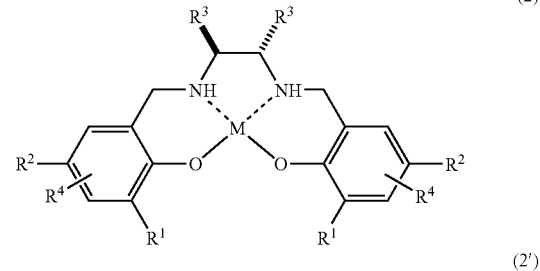

(2)

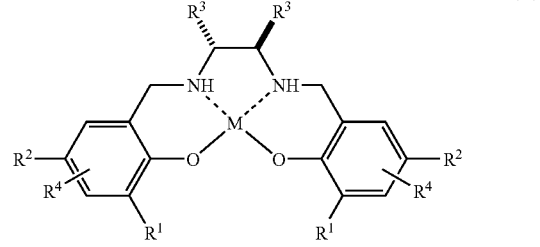

(2')

-continued

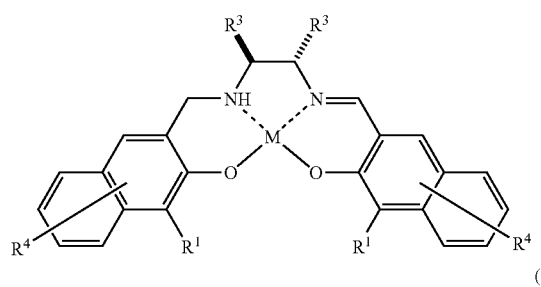
(3)

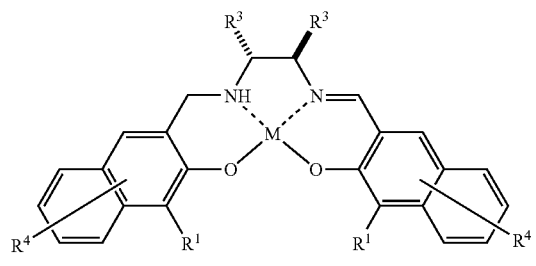
(3')

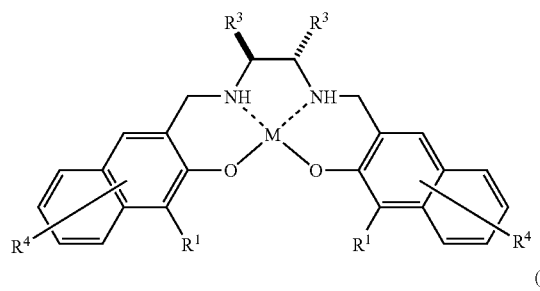
(4)

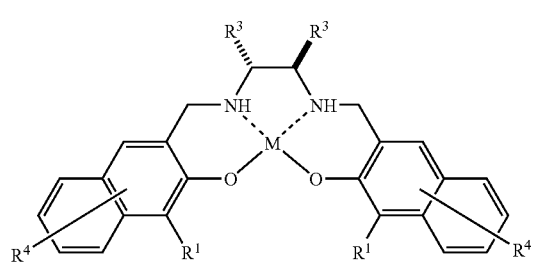
(4')

(where in Formula (1), Formula (1'), Formula (2), Formula (2'), Formula (3), Formula (3'), Formula (4) and Formula (4'), $R^1$ is a hydrogen atom, a halogen atom, a $C_{1-4}$ alkyl group, a $C_{1-4}$ alkoxy group, a $C_{6-12}$ aryloxy group or a $C_{6-22}$ aryl group (the aryl group is substituted with a $C_{1-4}$ alkyl group (the alkyl group is optionally substituted with a halogen atom), a $C_{1-7}$ alkoxy group or a benzyloxy group, and is optically active or optically inactive); $R^2$ is a hydrogen atom, a halogen atom, a $C_{1-4}$ alkyl group, a $C_{1-4}$ alkoxy group, a $C_{6-12}$ aryloxy group or a $C_{6-18}$ aryl group; $R^3$ is a $C_{1-4}$ alkyl group, a $C_{6-18}$ aryl group, or a $C_{3-5}$ divalent group when two $R^3$s together form a ring; $R^4$s are each independently a hydrogen atom, a halogen atom, a $C_{1-4}$ alkyl group, a $C_{1-4}$ alkoxy group, a nitro group or a cyano group; and M is TiJ$^1$J$^2$ (in TiJ$^1$J$^2$: Ti is a titanium atom; J$^1$ and J$^2$ are each independently a halogen atom or $C_{1-4}$ alkoxide, J$^1$ and J$^2$ together are an oxygen atom, or J$^1$ and J$^2$ together form a ring to form a binuclear complex of Formula (5):

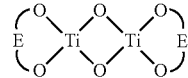
(5)

(where a partial structural formula O-E-O in Formula (5) is a formula of any one of Formula (6), Formula (6'), Formula (7), Formula (7'), Formula (8), Formula (8'), Formula (9) and Formula (9'):

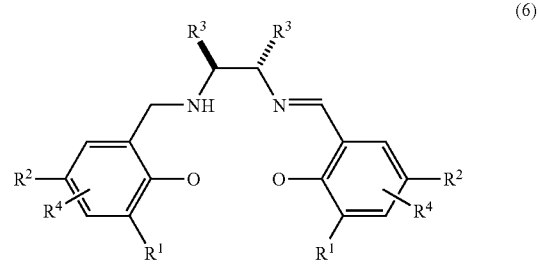
(6)

(6')

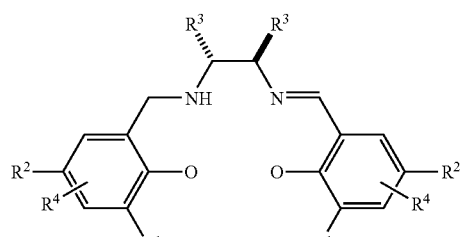
(7)

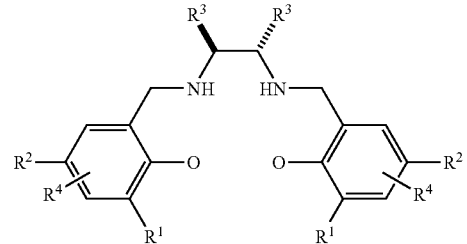
(7')

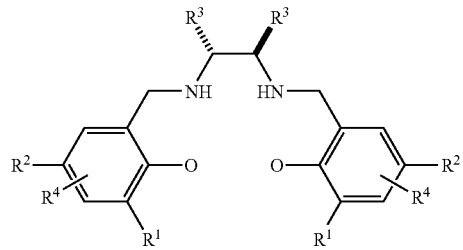
(8)

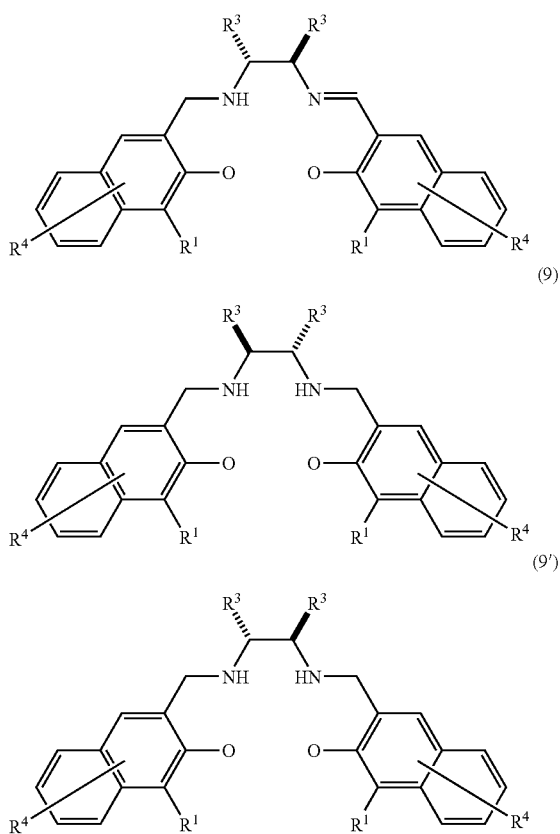

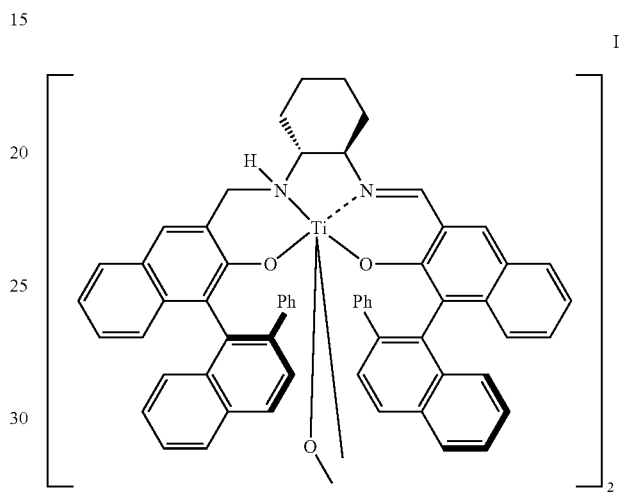

(where $R^1$, $R^2$, $R^3$ and $R^4$ in Formula (6), Formula (6'), Formula (7), Formula (7'), Formula (8), Formula (8'), Formula (9) and Formula (9') are the same as those defined above, and at this time, two partial structures O-E-O in Formula (5) are the same as each other))).

2. The production method of an optically active cis-silylolefin oxide compound according to claim 1, wherein
the optically active titanium complex of any one of Formula (1), Formula (1'), Formula (2), Formula (2'), Formula (3), Formula (3'), Formula (4) and Formula (4') is an optically active titanium complex of any one of Formula (1), Formula (1'), Formula (2) and Formula (2'),
$R^1$ is a phenyl group (the phenyl group is optionally substituted with a $C_{1-4}$ alkyl group (the alkyl group is optionally substituted with a halogen atom), a $C_{1-7}$ alkoxy group or a benzyloxy group),
$R^2$ is a hydrogen atom, and
two $R^3$s together are a $C_4$ divalent group.

3. The production method of an optically active cis-silylolefin oxide compound according to claim 1, wherein
the optically active titanium complex of any one of Formula (1), Formula (1'), Formula (2), Formula (2'), Formula (3), Formula (3'), Formula (4) and Formula (4') is an optically active titanium complex of any one of Formula (3), Formula (3'), Formula (4) and Formula (4'),
$R^1$ is a naphthyl group (the naphthyl group is optionally substituted with a $C_{1-4}$ alkyl group (the alkyl group is optionally substituted with a halogen atom), a $C_{1-7}$ alkoxy group or a benzyloxy group, and is optically active or optically inactive),
$R^2$ is a hydrogen atom, and
two $R^3$s together are a $C_4$ divalent group.

4. The production method of an optically active cis-silylolefin oxide compound according to claim 1, wherein
n is 0, and
$R^5$ is a phenyl group (the phenyl group is unsubstituted or is substituted with a halogen atom, a $C_{1-4}$ alkyl group, a $C_{6-10}$ aryl group (the aryl group is unsubstituted or is substituted with a halogen atom, a $C_{1-4}$ alkyl group or a $C_{1-4}$ alkoxy group) or a $C_{1-4}$ alkoxy group).

5. The production method of an optically active cis-silylolefin oxide compound according to claim 1, wherein the optically active titanium complex is a complex of Formula 1:

or an enantiomer of the complex.

6. The production method of an optically active cis-silylolefin oxide compound according to claim 1, wherein the solvent to be used in the asymmetric epoxidation reaction is a halogen-based solvent, an aromatic hydrocarbon solvent, an ester solvent, an ether solvent, a nitrile solvent, an alcohol solvent or a mixture of these solvents.

7. The production method of an optically active cis-silylolefin oxide compound according to claim 1, wherein the solvent to be used in the asymmetric epoxidation reaction is methylene chloride.

8. The production method of an optically active cis-silylolefin oxide compound according to claim 1, wherein the oxidant to be used in the asymmetric epoxidation reaction is iodosobenzene, sodium hypochlorite, m-chloro-perbenzoic acid, Oxone (registered trademark of E.I. du Pont de Nemours and Company), hydrogen peroxide water, urea-hydrogen peroxide adduct (UHP), oxaziridine, N-methylmorpholine oxide (NMO), t-butyl hydroperoxide (TBHP), cumene hydroperoxide (CHP) or a mixture of these oxidants.

9. The production method of an optically active cis-silylolefin oxide compound according to claim 1, wherein the oxidant to be used in the asymmetric epoxidation reaction is hydrogen peroxide water, urea-hydrogen peroxide adduct (UHP) or a mixture of these oxidants.

10. The production method of an optically active cis-silylolefin oxide compound according to claim 1, wherein the oxidant to be used in the asymmetric epoxidation reaction is hydrogen peroxide water in a concentration of 1 to 100% by mass.

* * * * *